United States Patent [19]

Abe et al.

[11] Patent Number: 5,342,876
[45] Date of Patent: Aug. 30, 1994

[54] SPHERICAL GRANULES OF POROUS SILICA OR SILICATE, PROCESS FOR THE PRODUCTION THEREOF, AND APPLICATIONS THEREOF

[75] Inventors: Kiyoshi Abe; Kazuhiko Suzuki, both of Shibata; Hiroshi Ogawa; Masaichi Kikuchi, both of Nakajo, all of Japan

[73] Assignee: Misuzawa Industrial Chemicals, Ltd., Tokyo, Japan

[21] Appl. No.: 8,545

[22] Filed: Jan. 25, 1993

[30] Foreign Application Priority Data

Jan. 24, 1992 [JP] Japan .................. 4-032915
Dec. 3, 1992 [JP] Japan .................. 4-350493

[51] Int. Cl.$^5$ ............... C08K 3/36; C01B 33/12
[52] U.S. Cl. .................. 524/493; 523/223; 524/442; 524/443; 524/444; 524/456; 423/335; 423/339; 428/328; 428/330; 428/331; 264/15
[58] Field of Search ............ 523/223; 524/442, 443, 524/444, 450, 456, 492, 493, 847, 555; 264/15; 423/335, 336, 337, 338, 339, 340; 428/328, 330, 331

[56] References Cited

U.S. PATENT DOCUMENTS

| | | | |
|---|---|---|---|
| 2,883,347 | 4/1959 | Fisher et al. | 264/15 |
| 4,010,242 | 3/1977 | Iler et al. | 423/335 |
| 4,131,542 | 12/1978 | Bergna et al. | 210/656 |
| 4,239,675 | 12/1980 | Ferrigno | 523/223 |
| 4,615,741 | 10/1986 | Kobayashi et al. | 524/493 |
| 4,640,807 | 2/1987 | Afghan et al. | 423/339 |
| 4,752,458 | 6/1988 | Robinson | 423/335 |
| 4,837,253 | 6/1989 | Mansell et al. | 524/492 |
| 5,028,360 | 7/1991 | Ito et al. | 423/335 |
| 5,128,114 | 7/1992 | Schwartz | 423/335 |
| 5,236,683 | 7/1993 | Nakazawa et al. | 423/335 |

FOREIGN PATENT DOCUMENTS

| | | | |
|---|---|---|---|
| 0526590 | 6/1956 | Canada | 524/492 |
| 52-032899 | 8/1977 | Japan . | |
| 57-055454 | 11/1982 | Japan . | |
| 61-010019 | 1/1986 | Japan . | |
| 61-168520 | 7/1986 | Japan . | |
| 0062362 | 3/1989 | Japan | 524/493 |
| 0296711 | 12/1990 | Japan | 264/15 |
| 04015237 | 1/1992 | Japan . | |

*Primary Examiner*—Peter Szekely
*Attorney, Agent, or Firm*—Sherman and Shalloway

[57] ABSTRACT

A porous and spherical silica is recovered in high yields from a neutralized product of an alkali silicate obtained by using an acrylamide type polymer as a coagulation growing agent, and the above silica is reacted as a precursor with a metal compound of the Group II of periodic table in an aqueous medium to obtain amorphous or fine, laminar and crystalline porous and spherical silica or silicate granules having a high degree of true sphericality, a symmetrical grain size distribution and a refractive index over a range of from 1.4 to 1.7. The porous and spherical granules have a primary grain diameter of 0.3 to 30 μm as observed through an electron microscope, have an apparent specific gravity of from 0.05 to 0.5 g/ml, and are cheaply obtained in high yields, and can hence be used as a filler for various paints and resins. In particularly, the granules excellently disperse in the resins, have a refractive index close to those of the resins, are not crushed during the kneading with resins or extrusion, or do not damage the apparatus. The films obtained by using these granules exhibit very excellent transparency, anti-blocking property and scar resistance. Moreover, the porous and spherical zinc phyllosilicate type granules having fine grain sizes and symmetrical grain size distributions, are excellent in their odor scavenging property and sweat controlling property.

21 Claims, 14 Drawing Sheets

SPHERICAL GRANULES OF POROUS SILICA OR SILICATE, PROCESS FOR THE PRODUCTION THEREOF, AND APPLICATIONS THEREOF

BACKGROUND OF THE INVENTION (1) Field of the Invention

The present invention relates to porous spherical silica or silicate granules and to a process for the production thereof. More specifically, the invention relates to true spherical porous granules of silica or silicate of a metal of Group II of periodic table, and to a process for the production thereof. The invention further relates to functional fillers such as an anti-blocking agent, a deodorizing agent, an odor scavenging agent and a sweat-controlling agent composed of the above spherical silica or silicate granules, that can be used for resins, fibers, paints and cosmetics.

(2) Description of the Prior Art

As fillers of the amorphous silica type, there have been known so-called dry-type silica and wet-type silica. Depending upon the properties, they have been used for such applications as paints, papers for recording information, rubbers, resin molded products and the like. The former silica is obtained by decomposing $SiCl_4$ in the flame of oxygen and hydrogen, has a small granular size and a spherical shape, and has a relatively small surface activity that stems from specific surface area, pore volume, pore distribution, etc. On the other hand, the latter silica is obtained by neutralizing alkali silicate with an acid, and generally has a large granular size and a wide granular size distribution, but its interior is porous and exhibits a relatively large surface activity. Thus, amorphous silica exhibits properties that greatly vary depending upon the preparation method. In the case of the latter wet-type silica, in particular, the reaction conditions such as concentration, pH, temperature, pressure and time for neutralizing alkali silicate with an acid can be variously changed, making it possible to obtain amorphous silica having widely different properties.

Among the amorphous silica fillers, it has been urged to provide amorphous silica granules of a regular shape such as fine spherical silica granules since they do not coagulate among the filler granules and exhibit excellent dispersing properties in the resins. Fine spherical silica granules have heretofore been produced by a method in which organic silane is hydrolyzed in an organic solvent such as ethanol, a method in which a silica sol or gel is formed in a spherical shape, a method in which a W/O emulsion is prepared from an aqueous solution of alkali silicate and an organic solvent followed by hydrolysis, a method in which molten silica is formed in a spherical shape, and a method in which granules of various kinds of zeolites of a regular shape are treated with an acid. According to these methods, however, the starting materials are expensive, and the aforementioned demand is not fully satisfied.

U.S. Pat. No. 4,752,458 discloses a process for producing fine spherical silica by adding a solution of an acid to a solution of soluble silicic acid and further adding thereto an organic polymer solution of an alkali metal salt of alginic acid, an ammonium salt of alginic acid, a starch, a gelatin, a pectin, or a mixture thereof prior to forming a gel thereof.

It has further been attempted to blend various blending agents such as inorganic fillers comprising various silicates in addition to those of silica in order to impart a variety of functions to the resin molded articles such as films and the like. The blending agents can be roughly divided into those for improving chemical properties of the resins and those for improving physical properties of the resin molded articles. The former agents include a heat stabilizer which suppresses the hydrogen chloride-removing reaction of chlorine-containing polymers and a stabilizer which suppresses the deterioration caused by a catalyst residue of a halogen compound contained in olefin type resins, and the latter agents include an anti-blocking agent for preventing the stretched resin film from being blocked and an agent for removing odor from a resin.

It has long been known to use silicates such as calcium silicate as a blending agent for improving chemical properties or a blending agent for improving physical properties. For instance, Japanese Patent Publication No. 32899/1977 discloses blending a chlorine-containing polymer with a synthetic calcium silicate as a thermostabilizer.

Moreover, Japanese Patent Laid-Open Publication No. 15237/1992 discloses a blending agent for resins comprising a fine crystalline calcium silicate hydrate.

Japanese Patent Laid-Open No. 10019/1986 discloses that a synthetic fine crystalline zinc silicate of the sauconite type, hemimorphite type or willemite type is useful as a blending agent for developers and resins.

SUMMARY OF THE INVENTION

The above prior art related to spherical silica are excellent in their idea of directly producing fine spherical granules by adding water-soluble organic polymer in a step of neutralizing alkali silicate with an acid. When the water-soluble organic polymers are added, however, the yield of the obtained fine spherical granules is as small as about 40% or lower. Even in the case where the yield is relatively high, there are produced large proportions of granules without regular shapes or having varying diameters. Moreover, the filtering property is very poor and practicability is very low.

The present inventors have discovered the fact that fine spherical granules of a partly neutralized product of an alkali silicate are precipitated in a good yield if water-soluble organic polymer or particularly if an acrylamide polymer is added in the step of neutralizing a solution of an alkali silicate with an acid.

That is, the object of the present invention is to provide a process for producing amorphous silica of a spherical shape, which enables fine spherical silica to be precipitated in good yield in the step of neutralizing an alkali silicate with an acid.

Another object of the present invention is to provide a process for producing spherical amorphous silica of a regular shape which is a spherical or a nearly spherical shape and having a symmetrical grain size distribution maintaining a high productivity and at a reduced cost.

A further object of the present invention is to provide amorphous silica granules comprising porous and amorphous silica having a distinctly spherical shape as a whole as well as a high refractive index, and having apparent densities lying over a wide range.

According to the present invention, there is provided a process for producing porous, spherical and amorphous silica granules comprising mixing an aqueous solution of an alkali silicate, an acrylamide polymer and an aqueous solution of an acid of a partly neutralizing amount together, leaving the mixed solution to stand to form a granular material composed of a partly neutralized product of the alkali silicate, and separating the granular material followed by neutralization with an acid.

According to the present invention, furthermore, there are provided porous and spherical silica granules comprising amorphous silica with a BET specific surface area of from 100 to 800 m²/g, more than 80% of the granules having a distinctly spherical shape as a whole and further having a true sphericality expressed by a ratio $D_S/D_L$ of a long diameter $D_L$ to a short diameter $D_S$ of the particles that will be described later of from 0.90 to 1.00, and the granules further having a sharpness of granular size distribution defined by the relation.

$$D_{25}/D_{75} \tag{1}$$

wherein $D_{25}$ denotes a grain diameter of 25% value on a volume-based cumulative grain size distribution curve as measured by the Coulter counter method, and $D_{75}$ demotes a grain diameter of 75% value thereof,
of from 1.2 to 2.0, and a refractive index of from 1.46 to 1.50.

The present invention is based on a discovery that among various water-soluble organic polymers acrylamide polymers singularly act as a coagulation growing agent for growing a partly neutralized product of alkali silicate into a granular material from the stand point of yield and maintaining a regular shape of granular material.

Table 1 appearing later shows the measured results of granular shape and grain diameter of a granular material and a yield (reckoned as $SiO_2$) of a partly neutralized product of alkali silicate that precipitates when an aqueous solution of sodium silicate, various water-soluble organic polymer solutions and sulfuric acid of a partly neutralizing amount are mixed together to prepare a transparent mixture solution, and when this mixture solution is left to stand at a temperature of 20° C. for 14 hours.

The results of this Table 1 tell the astonishing fact that the yield is as small as about 40% or smaller not only when use is made of sodium alginate, starch or gelatin that are described in the aforementioned prior art but also when use is made of nonionic water-soluble organic polymer such as polyvinyl alcohol (PVA) or polyethylene glycol (PEG), anionic water-soluble organic polymer such as carboxymethyl cellulose (CMC) or sodium polyacrylate (does not form spherical shape though not described in Table 1), or cationic water-soluble organic polymer such as a polyamine high molecular weight coagulating agent. Or, even when the yield is relatively high, the filtering property is very poor and the granules have poor spherical shapes and varying diameters. However, when acrylamide polymer is added, the yield is as great as 70% or more, and the granules have a good spherical shape and diameters that lie within a predetermined range.

FIG. 1 is a scanning electron microphotograph (magnification, 10000 times) showing granular structure of granular amorphous silica according to the present invention, from which it will be understood that the granules have a nearly uniform spherical shape.

FIGS. 2 and 3 show volume-based and number-based granular size distribution curves of granular amorphous silica according to the present invention, from which it will be understood that the granular amorphous silica of the present invention has a symmetrical grain size distribution which is close to single dispersion.

Generally, the degree of symmetry in the grain diameter (grain size) can be evaluated in term of a ratio $D_{25}/D_{75}$ of a grain diameter ($D_{25}$) corresponding to 25% of the integrated value on a cumulative grain size distribution curve to a grain diameter ($D_{75}$) corresponding to 75% of the integrated value on the same curve. That is, the smaller this value, the narrower the grain size distribution and the larger this value, the wider the grain size distribution.

The granular amorphous silica of the present invention has a ratio $D_{25}/D_{75}$ of smaller than 2.0 and, particularly, smaller than 1.6 in the volume-based distribution, the granular sizes being symmetrically distributed.

The true sphericality of the spherical granules can be evaluated in terms of a ratio $D_S/D_L$ of a long diameter $D_L$ to a short diameter $D_S$ on the cross section (projected plane) of the particles. More than 80% of the granular amorphous silica of the present invention has the true sphericality $D_S/D_L$ within a range of from 0.95 to 1.00, which is very superior to those to which other high molecular weight additives are added.

It is considered that the granular material composed of a partly neutralized product of alkali silicate of the present invention is creating a fine structure in which spherical primary particles of a size of silica sol are agglomerated in the form of clusters of grapes with polymer chains of acrylamide type polymer as cores. FIG. 4 schematically shows the fine structure inside this granular material. It is considered that the acrylamide polymer and primary particles that the acrylamide polymer and primary particles of silica are bonded together through hydrogen between the amide group and the silanol group on the silica surface as represented by the formula

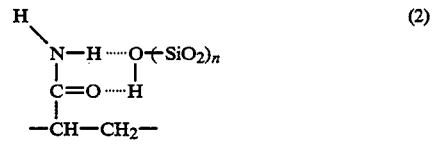

wherein n denotes an amount of silica that is allowed to exist as particles of a sol size.

An excellent coagulation growing action of the acrylamide polymer of the present invention can be obtained.

According to the present invention, the fact that the acrylamide polymer is contained in the neutralized product composed of partly neutralized product of alkali silicate can be confirmed from the fact that if the neutralized product is neutralized with an acid, the acrylamide polymer is extracted from the particles together with an alkali component contained therein. Even at the time of neutralization with an acid, the granular material that is once formed maintains its form while components other than the amorphous silica are removed. Therefore, the granular silica is obtained in a high yield maintaining a favorable spherical and granular shape and a sharp grain size distribution.

As described above, the spherical amorphous silica of the present invention consists of an aggregate of silica primary particles and has a relatively large BET specific surface area which is from 100 to 800 m²/g and, particularly, from 150 to 600 m²/g, has a degree of aggregation which is more dense than that of silica gel or the like, has a refractive index at 25° C. of as large as from 1.46 to 1.50, and an apparent specific gravity (g/ml) over a range which is as wide as from 0.15 to 0.6, thus presenting distinguished features.

The silicate particles such as calcium silicate or the like exhibit good pigment properties, can be blended and dispersed well in resins, react with hydrogen chloride and with chlorine ions to trap them, and further form protuberances on the film surface to improve anti-blocking property and slipping property, but still have defects that must be improved as described below.

(i) The silicates exhibit properties like those of a polishing agent though the degree may not be the same, and form scars on films. (ii) The synthetic silicates have a fine primary particle diameter and its aggregate, i.e. secondary particles, have unstable granular shapes and a broad grain size distribution, i.e. the synthetic silicate generally has neither spherical shape nor narrow granular size distribution. (iii) Among the synthetic silicate granules, those that give less scars have such a tendency that the secondary granules will be destroyed when they are kneaded with a resin. On the other hand, the granules in which the secondary particles are not likely to be destroyed tend to give scars to the dies during molding or tend to scar the film when the film is being produced. (iv) Many of the silicates tend to increase the haze of a resin composition which is blended therewith and to decrease the transparency.

According to the present invention, a true spherical silicate was successfully produced by using, as a precursor, a spherical silica obtained by neutralizing with an acid a mixture of the aforementioned aqueous solution of an alkali silicate and an acrylamide polymer, and by reacting this amorphous silica with a hydroxide or a salt of a metal of the Group II of periodic table in an aqueous medium. It was found that the above-mentioned defects (i) to (iv) are effectively overcome by the spherical silicate granules.

That is, the object of the present invention is to provide porous granules of a silicate of a metal of the Group II of periodic table having a distinctly spherical shape and a high degree of true sphericality, and a process for producing the same.

Another object of the present invention is to provide porous and spherical silicate granules that are not destroyed even when they are kneaded with resins, that do not give scars due to friction when films are being produced, and that exhibit excellent transparency, and to a process for the synthesis thereof.

A further object of the present invention is to provide a silicate-type anti-blocking agent or a resin blending agent comprising the above spherical silicate granules and having excellent dispersing property in the resins, reduced friction tendency with respect to the apparatus, excellent scar resistance on the film surface, improved transparency and excellent anti-blocking tendency, and deodorizing and odor scavenging actions.

According to the present invention, there are provided spherical silicate granules comprising porous granules of a silicate having a composition $SiO_2$:-$MO=99:1$ to $50:50$ (wherein M denotes a metal of the Group II of periodic table) expressed by a weight ratio based on oxides, having an amorphous or fine laminar crystalline property as viewed by the X-ray diffraction method, having a distinctly spherical shape as a whole and a true sphericality expressed by a ratio $D_S/D_L$ of a long diameter $D_L$ to a short diameter $D_S$ of the granules of from 0.8 to 1.0, and a grain diameter of from 0.3 to 20 μm as observed through a scanning electron microscope.

According to the present invention, furthermore, there is provided a process for producing spherical silicate granules comprising reacting a granular material composed of a partly or completely neutralized product of alkali silicate obtained by using an acrylamide polymer as a coagulation growing agent with a hydroxide or a salt of a metal of the Group II of periodic table in an aqueous medium.

According to the present invention, the granular material of a partly or completely neutralized product of alkali silicate is obtained by mixing an aqueous solution of an alkali silicate, an acrylamide polymer and a partly neutralizing amount of an aqueous solution of an acid together, and leaving this mixture solution to stand to form a granular material composed of a partly neutralized product of alkali silica, or further neutralizing the granular material with an acid.

In the present invention, a distinguished feature resides in that the silicate granules comprise porous and spherical granules having a composition $SiO_2$:-$MO=99:1$ to $50:50$ (wherein M is a metal of the Group II of periodic table) expressed by a weight ratio based on oxides, yet having a distinctly spherical shape and a true sphericality of as great as 0.8 or higher, and grain diameters over a predetermined range of from 0.3 to 20 μm as observed through a scanning electron microscope.

In the present invention, the individual silicate particles have independent and distinctly true spherical shape making a distinguished difference from the conventional silicates of a metal of the Group II of periodic table that are amorphous as observed through an electron microscope. The spherical granules usually have grain diameters within a predetermined range of from 0.3 to 20 μm which are suited for being blended to impart anti-blocking property to resins.

The accompanying FIG. 11 is a scanning electron microphotograph of the spherical silicate granules according to the present invention from which it will be recognized that the granules have a true sphericality with their grain sizes lying within the above-mentioned predetermined range.

The individual silicate particles have independent spherical shapes and exhibit an excellent dispersing property in resins. Moreover, since the sphere has the smallest surface area per unit weight, the granules are excellently wet with a resin, and form a rugged film surface to impart anti-blocking property without being exposed to the film surface. Even when exposed to the film surface, the granules having spherical surfaces exhibit excellent slipping property and the granules are not likely to be destroyed.

The accompanying FIG. 12 is an electron microphotograph measuring the dispersing condition of the spherical silicate granules in a film based on the ash content when the film is formed by kneading the spherical silicate granules of the invention and a polypropylene together (the measuring method will be described later in detail), and FIG. 13 is an electron microphotograph measuring, based on the ash content, the dispersing condition in the film of spherical amorphous silica which is a precursor of the spherical silicate granules. It becomes obvious from FIGS. 12 and 13 that the silicate of the present invention helps to increase the grain strength and to prevent the grains from being destroyed (the reasons will be described later).

Besides, the spherical silicate granules of the present invention are porous which is another feature. The porosity of granules can be evaluated by a pore volume based on the nitrogen absorption method. The porous spherical silicate granules of the present invention have a peak of pore volume usually in the pore radii of from 10 to 100 Å, and further have a pore volume of from 0.2 to 2.0 cm$^3$/g and, particularly, from 0.3 to 1.0 cm$^3$/g.

The silicate granules of the present invention are porous. That is, the surfaces are relatively soft, spherical and are porous but are not abrasive. Therefore, the silicate granules of the invention offer excellent scar resistance and granular shape retentivity in combination.

In the present invention, it is also important that the silicate granules contain $SiO_2$ and a metal component (MO) of the Group II of periodic table at the aforementioned weight ratio and, preferably, at a weight ratio of from 99:1 to 50:50. When the weight ratio of MO is either smaller than or greater than the above ratio, the transparency tends to be deteriorated when they are blended in a resin and, besides, it becomes difficult to maintain a balance between the scar resistance of the resin film and the grain strength. The silicate granules of the present invention exhibit a refractive index which is generally close the refractive indexes of various resins, i.e., from 1.47 to 1.55 and, particularly, from 1.48 to 1.53 as measured by the solution immersion method.

Moreover, the spherical and porous granules have a small weight per granule, a symmetrical grain size distribution and resistance against destruction. Therefore, even when blended in small amounts in the resins, the spherical and porous granules effectively impart anti-blocking property as well as deodorizing and odor scavenging actions which are excellent advantages that are not quite recognized in the conventional anti-blocking agents.

The process for preparing porous and spherical silicate granules of the present invention comprises reacting in an aqueous medium a hydroxide or a salt of a metal of the Group II of periodic table with spherical granules composed of a partly or completely neutralized product of an alkali silicate obtained by using an acrylamide polymer as a coagulation growing agent.

Amorphous silica is formed by neutralizing an alkali silicate with an acid. Here, if an acrylamide polymer is made present in the partly neutralized material of alkali silicate, the partly neutralized material grows into a granular material having a high degree of true sphericality and symmetric grain size distribution maintaining a good yield. According to the present invention, the granular material or a completely neutralized product thereof is reacted with a hydroxide or a salt of a metal of the Group II of periodic table in an aqueous medium to produce porous and spherical silicate granules.

The granular amorphous silica used as the precursor (sample 1–2) of the present invention has a nearly uniform spherical shape as shown in FIG. 16, and has a symmetrical grain size distribution which is close to single dispersion as shown in FIGS. 17 and 18.

The granular amorphous silica used in the present invention has the aforementioned ratio $D_{25}/D_{75}$ of smaller than 2.0 and, particularly, smaller than 1.6 in the volume-based distribution, and has a symmetrical grain size distribution.

As described earlier, furthermore, the true sphericality of the spherical grains can be evaluated in terms of a ratio $D_S/D_L$ of a long diameter $D_L$ to a short diameter $D_S$ on the cross section (projected plane) of granules. According to the present invention, the true sphericality ($D_S/D_L$) of the silicate granules lies within a range of from 0.80 to 1.00 because of the fact that the true sphericality ($D_S/D_L$) of the granular amorphous silica which is a precursor used in the present invention lies within a range of from 0.80 to 1.00 which is markedly superior to that of the granular material obtained by adding other aqueous organic polymers.

In the present invention, spherical granules composed of a partly or completely neutralized material of an alkali silicate are reacted with a hydroxide or a salt of a metal of the Group II of periodic table in the presence of an aqueous medium, whereby the hydroxide or the salt enters into voids among silica primary particles and a silicate is formed upon the reaction starting from the surface of the silica primary particles. Upon the formation of the silicate, the bonding among the primary particles becomes stronger and resistance against destruction of the particles is markedly improved while maintaining the granular structure and the porous structure of the granular material composed of a partly or completely neutralized material of an alkali silicate which is used as the precursor. According to the present invention, a distinguishing feature resides in that a balance between the grain strength (non-destructiveness) and scar resistance can be set over a suitable range by changing the ratio of reaction quantity of a metal component of the Group II of periodic table.

The porous silicate granules of the present invention exist in the form of an amorphous of fine crystalline laminar phyllosilicate as observed by an X-ray diffraction method. The accompanying FIG. 14 shows an X-ray diffraction image of a typical amorphous example (calcium silicate) and FIG. 15 shows an X-ray diffraction image of a typical laminar fine crystalline example (magnesium phyllosilicate). Moreover, a zinc phyllosilicate and an aluminum-containing zinc phyllosilicate in which the metal (M) of the Group II is zinc, are similarly laminar fine crystalline silicates. This means that in the silicate granules of the present invention, there is no regularity of bonds between the silica and the metal oxide or no regularity or very little regularity in the lamination of basic silicate layers, which is also related to the porous structure.

Moreover, the spherical and porous granules have a small weight per granule, a symmetrical grain size distribution and resistance against destruction. Therefore, even when blended in small amounts in resins, the spherical and porous granules effectively impart anti-blocking property as well as deodorizing, odor scavenging and sweat controlling actions which are excellent advantages that are not recognized in the conventional anti-blocking agents.

DETAILED DESCRIPTION OF THE PREFERRED EMBODIMENTS

Figure 5:
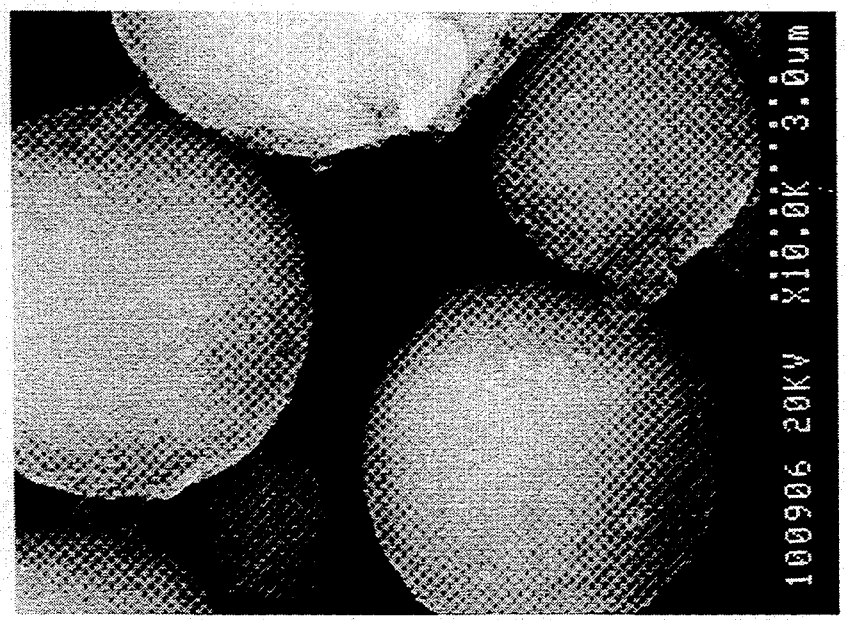
FIG. 5 is a scanning electron microphotograph of a magnification of 10,000 times showing the granular structure of fine spherical silica granules obtained in Example 4 of the present invention.

For easy comprehension of the porous silica or silicate spherical granules of the present invention, the preparation methods will be described below. (Alkali silicate)

As an alkali silicate, use is made of an aqueous solution of an alkali silicate and, particularly, of a sodium silicate having a composition represented by the formula, $$Na_2O \cdot mSiO_2 \quad (3)$$

wherein m is a number of 1 to 4 and, particularly, 2.5 to 3.5.

The composition of the alkali silicate has a relation to the stability of the mixture solution and to the yield and grain size of the granular material that is formed. When the mol ratio (m) of $SiO_2$ is smaller than the above range, the partly neutralized particles precipitate difficulty, the yield decreases, the granular shape and granular form become nonuniform and, besides, acid is required in an increased amount for effecting the partial neutralization. When the mol ratio of $SiO_2$ becomes greater than the above range, on the other hand, the mixture solution loses stability, the granular form loses true sphericality, and the grain size distribution loses sharpness.

The concentration of alkali silicate should be such that the concentration of $SiO_2$ is from 3 to 9% by weight and, particularly, from 5 to 8% by weight in the mixture solution.

Acrylamide polymer

The acrylamide polymer used in the present invention as a silica granule coagulation growing agent includes an acrylamide recurring unit represented by the formula,

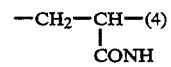

(4)

It is desired that the acrylamide polymer is a single polymer of acrylamide. Within a range in which the acrylamide recurring unit constitutes more than 70 mol % and, particularly, more than 90 mol % of the whole amount, however, the acrylamide polymer may further contain recurring units of a monomer which is copolymerizable therewith such as ethylenically unsaturated carboxylic acids like acrylic acid, methacrylic acid, maleic acid, or fumaric acid, or vinyl ethers, or (meth)acrylic acid esters. The acrylamide polymer may further contain an anionic unit which is modified into a carboxyl group upon hydrolysis or a cationic unit which is esterified with an aminoalkyl group or with a quaternary ammonium alkyl group.

The acrylamide polymer used in the present invention should not have a large molecular weight, and its weight average molecular weight ($\overline{M}_W$) should generally be from 10,000 to 3,000,000 and, particularly, from 100,000 to 2,000,000. When the molecular weight of the acrylamide polymer becomes too great, it becomes difficult to form and precipitate the granular material. This is presumed to be due to the fact that when the molecular weight becomes too great, the molecular chains intermingle with each other in large amounts making it difficult to create the aforementioned clustered aggregate structure.

In the acrylamide polymer, the relationship between the weight average molecular weight ($M_W$) and the intrinsic viscosity ($\eta$) is expressed by the following formula, $$\eta = 3.73 \times 10^{-4} \times (M_W)^{0.66} \quad (5)$$

where the intrinsic viscosity $\eta$ is measured in a 1N sodium nitrate solution at 30° C.

The acrylamide polymer preferably used in the present invention contains a carboxyl group which is free or in the form of a salt at a concentration of 0.2 to 50 millimol and, particularly, 0.5 to 20 millimole per 100 g of the polymer. It is considered that the anionic groups in the polymer chains work to stretch the molecular chains in water due to electrostatic repulsive force of groups having the same polarity, facilitating the formation of the clustered aggregate structure of the silica primary particles.

It is desired that the acrylamide polymer is added in an amount of 5 to 100% by weight and, particularly, 10 to 50% by weight based on $SiO_2$. When the amount is smaller than the above range, the granular material is not precipitated in a good yield and when the amount is greater than the above range, no distinguished merit is obtained while giving a disadvantage to the economy.

Acid

A variety of inorganic acids and organic acids can be used. From the economical point of view, however, it is desired to use a mineral acid such as sulfuric acid, hydrochloric acid, nitric acid or phosphoric acid. Among them, sulfuric acid is most desirable with respect to the yield of the granular material and uniformity in the grain diameter and grain form.

In order to carry out homogeneous reaction, it is desired to use the acid in the form of a dilute aqueous solution usually at a concentration of from 1 to 15% by weight. A neutral salt may be added to the acid. The acid should be mixed in such an amount that a homogeneous mixture solution (transparent) is formed upon partial neutralization, i.e., in such as amount that the pH of the mixture solution is from 10.2 to 11.2 and, particularly, from 10.5 to 11.0.

Precipitation of granular material

In the present invention, there is no particular limitation in the order of adding the above-mentioned components. For instance, the acrylamide type polymer may be added after the acid has been added to the aqueous solution of alkali silicate. Or, conversely, the acid may be added after the acrylamide type polymer has been added to the aqueous solution of alkali silicate. They may be added simultaneously, as a matter of course.

After the components are sufficiently mixed and homogenized, the mixture solution is left to stand still, so that the granular material of the partly neutralized product is precipitated.

The condition of precipitation usually consists of leaving the mixture solution to stand at a temperature of from 1° to 100° C. for about 1 to about 50 hours. In general, the grain diameter of the precipitated granules increases with a decrease in the temperature, and the grain diameter of the precipitated granules decreases with an increase in the temperature. Thus, the granular material is controlled by controlling the temperature, providing one of the advantages of the present invention.

The precipitated granules and the mother liquor are separated from each other, the dispersed granules are neutralized by adding an acid, washed with water, dried, and classified to obtain a product. The separated mother liquor and the separated solution after neutralization contain an unprecipitated silica component and acrylamide polymer which can be effectively recycled for use the next time. (Granular amorphous silica)

As mentioned already, the granular amorphous silica according to the present invention has a BET specific surface area of 100 to 800 $m^2/g$, has a distinctly spherical shape, and in which more than 80% of the granules have a true sphericality expressed by a ratio $D_S/D_L$ of a long diameter $D_L$ to a short diameter $D_S$ of granules of from 0.90 to 1.00, and further has a sharpness of grain size distribution defined by a relation, $$D_{25}/D_{75} \qquad (1)$$

wherein $D_{25}$ denotes a grain diameter of 25% value on a volume-based cumulative grain size distribution curve as measured by the Coulter counter method, and $D_{75}$ denotes a grain diameter of 75% value thereof, of from 1.2 to 2.0, and a refractive index over a range of from 1.46 to 1.50.

As desired, furthermore, a metal soap, a resin acid soap, various resins or waxes, silane or titanium coupling agents, oxides or hydroxides of various metals, or silica coatings may be applied to the granular amorphous silica.

Precursor and its preparation method

The precursor used for the silicate of the present invention is a partly or completely neutralized product of an alkali silicate which is obtained by using the acrylamide polymer as a coagulation growing agent. Though there is no particular limitation, the precursor is usually obtained by forming a granular material composed of a partly neutralized product of alkali silicate and, as required, by neutralizing the granular material with an acid.

Therefore, the precursor just consists of the porous silica granules of the present invention, and is prepared under quite the same conditions for precipitating the above silica granules with the exception of the following.

i. Alkali silicate

The concentration of alkali silicate should be such that the concentration of $SiO_2$ is from 2 to 10% by weight and, particularly, from 4 to 8% by weight in the mixture solution.

ii. Acrylamide polymer

As the acrylamide recurring units, there can be added alginate, gelatine, polyvinyl alcohol, polyethylene glycol, pectin, starch, carboxymethyl cellulose, sodium polyacrylate and the like, in addition to the above.

iii. Acid

The acid should be used in such an amount that the pH of the mixture solution is from 10.0 to 11.2 and, particularly, from 10.2 to 11.0.

Reaction with a metal hydroxide or a salt of the Group II

According to the present invention, spherical granules comprising a partly or completely neutralized product of alkali silicate obtained by the above method are reacted with one or two or more kinds of hydroxides or salts of metals of the Group II of periodic table in the presence of an aqueous medium.

i. Hydroxide or salt

As metals of the Group II of periodic table, there can be cited magnesium, calcium, barium, strontium and zinc which can be used in the form of hydroxides or inorganic salts such as nitrates, chlorides or sulfates, or organic salts such as acetates, sulfonates, etc.

When the spherical granules used as the precursor are a completely neutralized product of alkali silicate, i.e., amorphous silica, it is desired to use a hydroxide. This is because with this combination, other impurity ions are not contained giving advantage from the standpoint of purity of the silicate and the operation of production.

When the spherical granules used as the precursor are a partly neutralized product of alkali silicate, on the other hand, it is desired to use a metal salt or a combination of a metal salt and a metal hydroxide as a starting material. This is because a double decomposition reaction takes place between the metal salt and the alkali silicate component remaining in the spherical granules, and the metal silicate is formed smoothly and efficiently. It is, of course, desired that a relationship of equivalence is maintained between the alkali component in the spherical granules and the acid radicals of the metal salt.

ii. Reaction condition

The granular material of a partly or completely neutralized product of alkali silicate should be reacted with the metal hydroxide at the above-mentioned ratio of amounts. The reaction should be carried out in an aqueous medium. When excess of alkali components or acid radicals exist in the reaction material, there can be added an acid or an alkali component in a corresponding amount to the aqueous medium.

There is no particular limitation in the reaction conditions provided the granular structure of the precursor is maintained and the silicate is formed. Usually, however, the reaction temperature ranges from 50° to 300° C. and, particularly, from 90° to 200° C., and the reaction time ranges from 0.5 to 100 hours and, particularly, from 2 to 8 hours.

During the reaction, the $SiO_2$ concentration in the aqueous medium should range from 2 to 30% by weight and, particularly, from 5 to 25% by weight. The order of the reaction may be one of a one-side pouring method in which a hydroxide or a salt of a metal is poured into an aqueous dispersion of the silica precursor, a simultaneous pouring method in which both starting materials are poured into the aqueous medium, or a simultaneous feeding method in which an aqueous medium in which two raw materials are dispersed is heated to a predetermined temperature.

The thus obtained spherical silicate granules of the present invention are separated from the reaction mother liquor by the solid-liquid separation method such as filtering and, as required, are washed with water, dried at a temperature of not higher than 150° C., or are calcined at a temperature of from 150° C. to 1000° C. With the calcining being effected, the specific surface area, pore volume or hygroscopic amount can be decreased accompanying the rise in the temperature.

Porous spherical silicate granules

The porous spherical silicate granules of the present invention have the chemical composition, crystallographic properties and granular structure that are described above already. As mentioned earlier, furthermore, the silicate granules have a variety of properties which can be set to any desired values within the aforementioned range by changing the kind of metal of the Group II of periodic table that is used and its amount.

Figure 19:
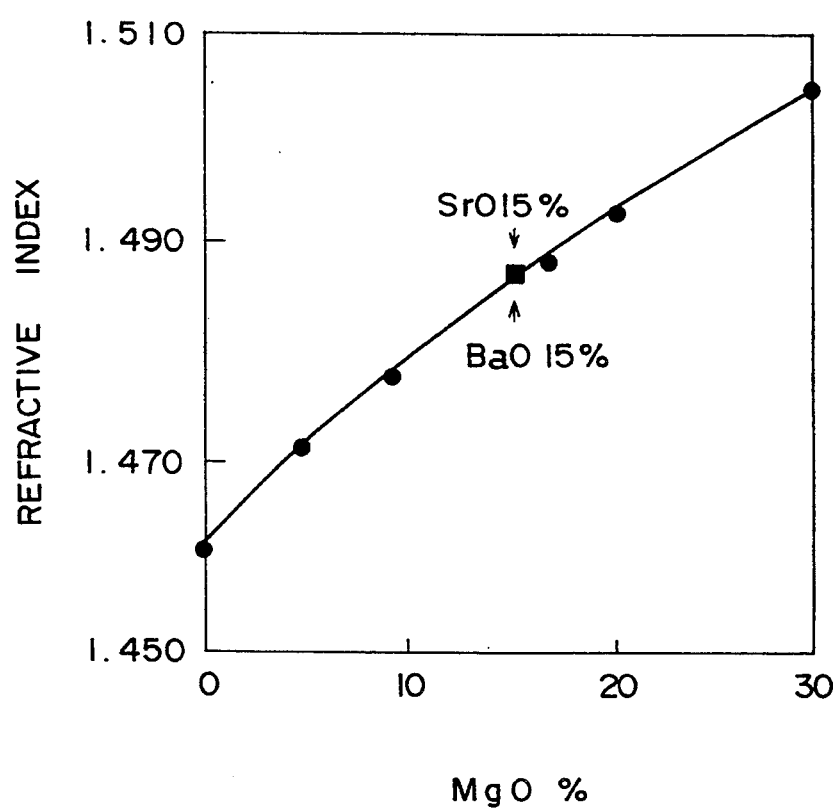
FIG. 19 is a diagram showing the amount of MgO added and a change in the refractive index.
Figure 20:
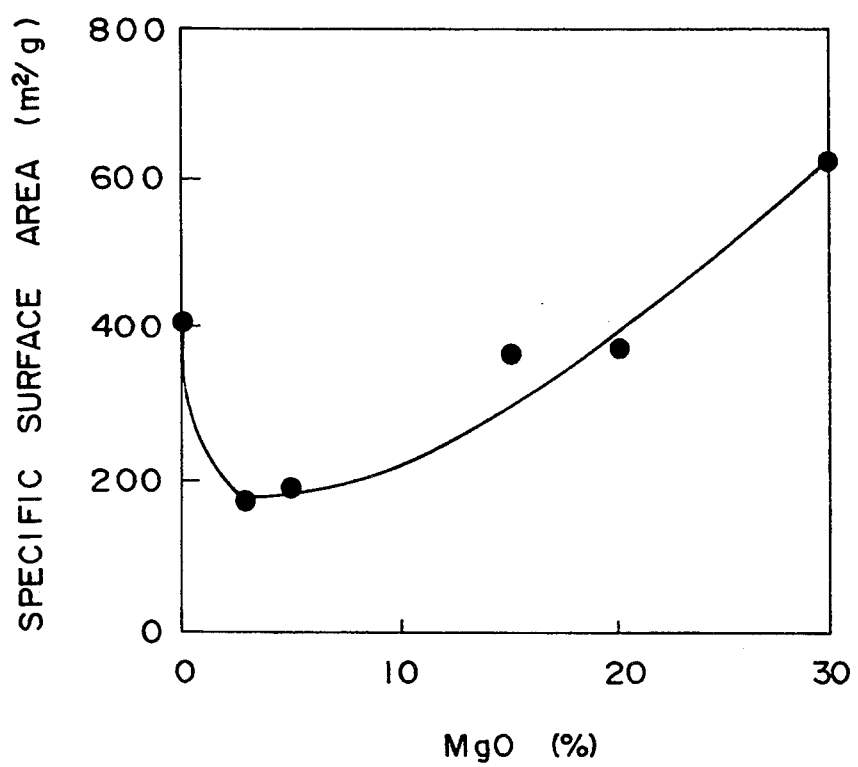
FIG. 20 is a diagram showing the amount of MgO added and a change in the BET specific surface area.

For instance, FIG. 19 shows the change in the refractive index of a silicate when the amount of magnesium hydroxide that is used is changed, and FIG. 20 shows the change in the BET specific surface area of the silicate when the amount of magnesium hydroxide is changed.

It will be understood from these results that the refractive index can be increased with an increase in the amount of the metal component of the Group II and that the specific surface area decreases to a certain level with an increase in the amount of the metal component of the Group II but the specific surface area increases again as the phyllosilicate is formed.

Figure 21:
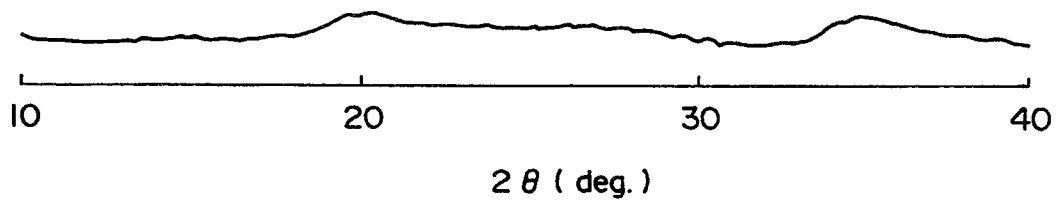
FIG. 21 is an X-ray diffraction diagram of a magnesium phyllosilicate.

Among the phyllosicate, it is desired that the porous spherical silicate granules of the present invention comprise a magnesium phyllosilicate, a zinc phyllosilicate and an aluminum-containing zinc phyllosilicate. The porous spherical silicate granules have an oleophilic property, disperse excellently in resins, and exhibit deodorizing and odor scavenging action. The phyllosilicate of the philloaluminosilicate containing a zinc component and a magnesium component have basic structures in which a tetrahedral layer of $SiO_4$ or $AlO_4$ or $SiO_4$ and an octahedral layer of $MO_6$ (M denotes Zn or a combination of Zn and Mg) are bonded in two layers or in three layers, and exhibit a strong adsorptive property to both the basic substances and acidic substances owing to the above laminar constitution. Phyllocalumino) silicates exhibit excellent adsorptive properties to various substances owing to chemical adsorption among the layers of a multi-layer structure. FIG. 21 is an X-ray diffraction image of a (magnesium) phyllosilicate which shows a feature of laminar crystals.

Figure 22:
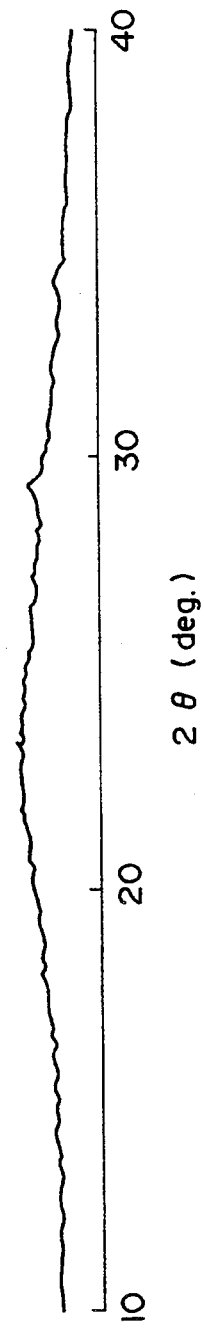
FIG. 22 is an X-ray diffraction diagram of a calcium silicate.
Figure 23:
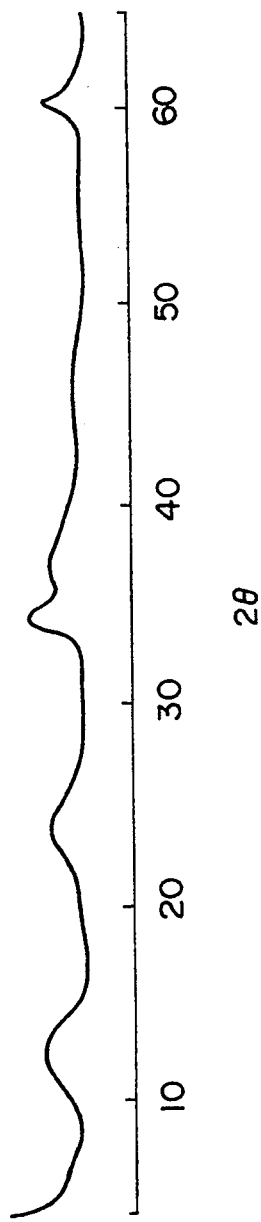
FIG. 23 is an X-ray diffraction diagram of aluminum-containing zinc phyllosilicate.

FIG. 22 is an X-ray diffraction image of a typical amorphous (calcium) silicate. Whether an amorphous phyllosilicate is formed or a fine crystalline phyllosilicate is formed is determined depending upon the starting materials and the reaction conditions. The magnesium component tends to form a phyllosilicate. Or, the phyllosilicate is formed even with other metal components under the hydrothermal synthetic conditions in which the temperature is higher than 120° C.

As mentioned already, the spherical silicate granules of the present invention have novel properties in combination and comprise an amorphous silicate having a BET specific surface area of from 50 to 800 m$^2$/g, a distinctly spherical shape as a whole, a true sphericality expressed by a ratio $D_S/D_L$ of a long diameter $D_L$ to a short diameter $D_S$ of granules of from 0.80 to 1.00, a sharpness of grain size distribution defined by a relation, $$D_{25}/D_{75}$$

wherein $D_{25}$ denotes a grain diameter of 25% value on a volume-based cumulative grain size distribution curve as measured by the Coulter counter method, and $D_{75}$ denotes a grain diameter of 75% value thereof,
of from 1.2 to 2.0, and a refractive index of from 1.47 to 1.55.

As desired, furthermore, a metal soap, a resin acid soap, various resins and waxes, saline type or titanium type coupling agents, oxides or hydroxides of various metals, and particularly, silica, iron and alumina coating may be applied to the spherical silicate granules.

Applications

By utilizing the above-mentioned properties, the porous spherical silica or silicate granules of the present invention can be blended into a variety of thermoplastic resins such as a homopolymer of propylene which is a crystalline propylene polymer an ethylene-propylene copolymer; olefin-type resins such as a low-, medium-, high-density or linear low-density polyethylene (linear low-density polyethylene (LLDPE) is a copolymer of an ethylene and one or two or more kinds of α-olefins(-propylene, butene-1, pentene-1, hexene-1, 4-methylpentene-1, octene-1, decene-1, etc.) with 4 to 18 carbon atoms); an ionically crosslinked olefin copolymer; an ethylene-vinyl acetate copolymer; an ethylene-acrylic acid ester copolymer; thermoplastic polyesters such as a polyethylene terephthalate (which can be added during the polymerization in addition to the resin alone) and polybutylene terephthalate; polyamide resins (which can be added during the polymerization in addition to the resin alone) such as 6-nylon, 6,6-nylon, 6,8-nylon; chlorine-containing resins such as vinyl chloride and vinylidene chloride; polycarbonates and polysulfonates; in order to form resin molded articles such as a variety of stretched, non-stretched and inflation films while imparting slipping property, anti-blocking property and deodorizing and odor scavenging functions to them.

For this purpose, the spherical silicate granules of the present invention are blended in an amount of from 0.01 to 10 parts by weight and, particularly, in an amount of from 0.02 to 3 parts by weight per 100 parts by weight of the thermoplastic resin.

Moreover, the porous spherical silica or silicate granules of the present invention can be used for a variety of applications, such as being blended into various paints, extender pigments for inks, in adhesives and coating resin compositions, and can further be used as a carrier or a filler for medicine, foods, agricultural chemicals and insecticides. Concretely speaking, they can be used for a fluidity improving agent for toners, a higher abrasive agent, a delustering filler, a carrier fluidity improving agent, a parting agent, a filler for rubbers, a base for ceramics, a powder foundation, a paste-like foundation, baby powder, a base for cosmetics such as creams, etc., a sweat-controlling agent, and a tooth paste.

EXAMPLES

The invention will now be described in detail by way of the examples. The properties of the porous and spherical silica or silicate granules were measured and evaluated in compliance with the following methods.

(1) Chemical composition

Measured in compliance with a method of analyzing silica stipulated under JIS M-8852.

(2) Apparent specific gravity

Measured in compliance with JIS K-6220.6.8.

(3) Oil-absorbing amount

Measured in compliance with JIS K-5101.19.

(4) Specific surface area, pore volume

Measured in compliance with the BET method by using the Sorptomatic Series 1800 manufactured by Carlo-Elba Co.

(5) Grain size

Measured by using aperture tubes 50 u in compliance with the Coulter counter method (Model TA-II, manufactured by Coulter Electronics Co.).

(6) Grain diameter by SEM

Typical granules are selected from a photographic image obtained by using a scanning electron microscope (S-570 manufactured by Hitachi, Ltd.), and diameters of granule image are measured by using a scale to find a primary granule diameter.

(7) True sphericality

Typical granules are selected from a photographic image obtained by using a scanning electron microscope (S-570 manufactured by Hitachi, Ltd.), and long diameters and short diameters of granule image are measured by using a scale to fined the true sphericality from the following relation, $$\text{True sphericality} = \text{short diameter } (D_S)/\text{long diameter } (D_L) \quad (6)$$

(8) Refractive index

By using the Abbe's refractometer, a solvent (α-bromonaphthalene, kerosine) having a known refractive index is prepared in advance. Then, in compliance with the Larsen's oil immersion method, several milligrams of a sample powder are placed on a slide glass, a drop of the solvent having a known refractive index is added thereto, a cover glass is placed thereon so that the sample powder is sufficiently immersed with the solvent, and the motion of Becke line is observed through an optical microscope to find the refractive index.

(9) Amount worn out

The amounts worn out are measured by using a Filcon-type abrasion tester (manufactured by Nippon Filcon Co.) under the following conditions.

| | |
|---|---|
| Rolls used | ceramics |
| Number of revolutions of rolls | 1500 rpm |
| Angle of contact | 111° |
| Size of test piece | 40 × 140 mm |
| Weight of test piece | about 2 g |
| Material of test piece | a plastic wire |
| Weight | 850 g |
| Concentration of solid component | 2% |
| Time for measurement | 180 min. |
| Expression of result | reduction of weight (mg) |

(10) Yield

The weight of the formed $SiO_2$ (fired at 860° C.) is divided by the whole amount of $SiO_2$ in the sodium silicate used in the reaction to find the yield according to the following relation, Yield (%) = [weight (g) of formed $SiO_2$/ amount (g) of the whole reacted $SiO_2$] × 100

EXAMPLE 1

Into a 2-liter stainless steel beaker were introduced 471 g of a solution of sodium silicate No. 3 (containing 22.3% of $SiO_2$ component and 7.0% of $Na_2O$ component) (7% of $SiO_2$ concentration in the whole solution) and 327 ml of pure water. The mixture was then introduced into a constant temperature bath adjusted at 20° C., followed by the addition of 300 g of an acrylamide polymer aqueous solution (about 10% aqueous solution, weight average molecular weight 500,000) with stirring such that the polyacrylamide reckoned as anhydride was 28% with respect to the whole $SiO_2$.

Then, 402 g of 7% sulfuric acid was added thereto (pH was 10.70 after sulfuric acid had been added). After the addition had been finished, the stirring was discontinued, and the mixture was left to stand still for 12 hours. The mixture was then filtered, and the obtained silica cake was dispersed again in pure water, and 7% sulfuric acid was added thereto with sufficient stirring until pH reached 3.0. Thereafter, the mixture was filtered, washed with water, dried at 110° C., pulverized in a sample mill, and was baked at 500° C. for 2 hours to obtain a fine granular and spherical silica powder.

Figure 1:
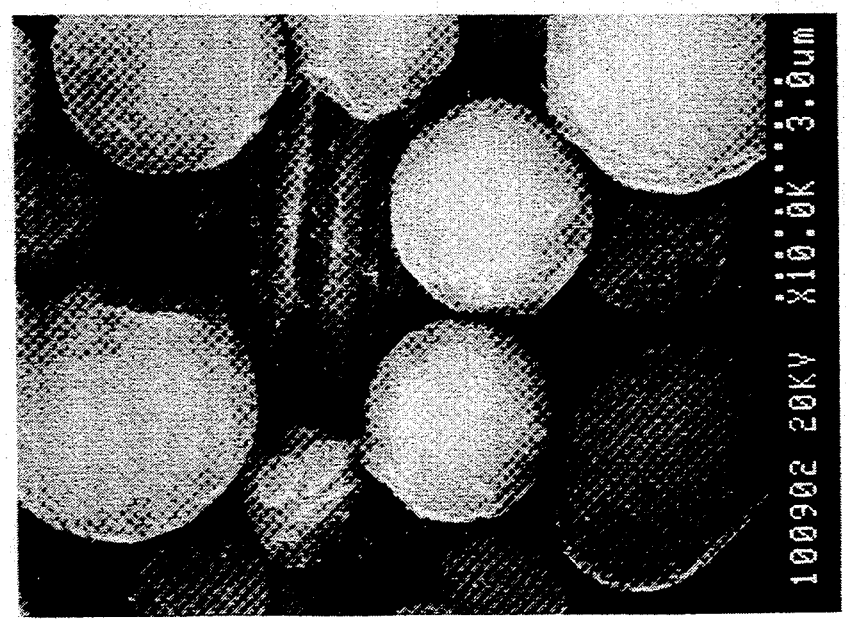
FIG. 1 is a scanning electron microphotograph of a magnification of 10,000 times showing the granular structure of a spherical silica obtained in Example 1 of the present invention.
Figure 2:
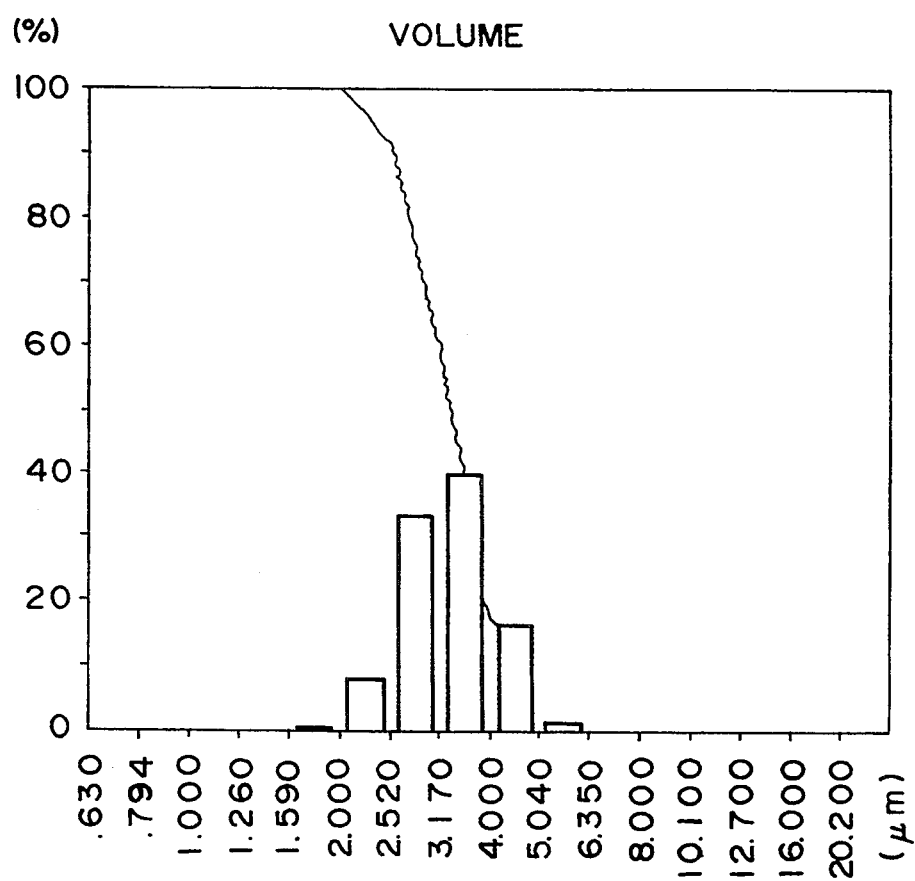
FIG. 2 is a volume-based grain size distribution curve of the spherical silica obtained in Example 1 of the present invention.
Figure 3:
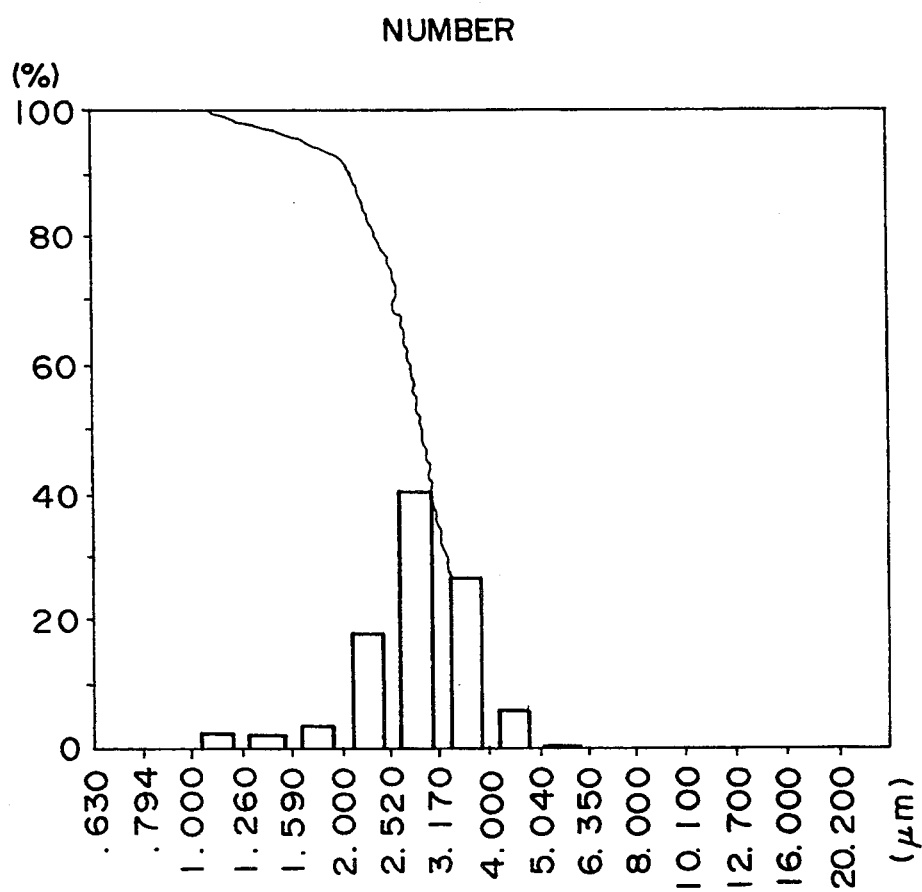
FIG. 3 is a number-based grain size distribution curve of the spherical silica obtained in Example 1 of the present invention.
Figure 4:
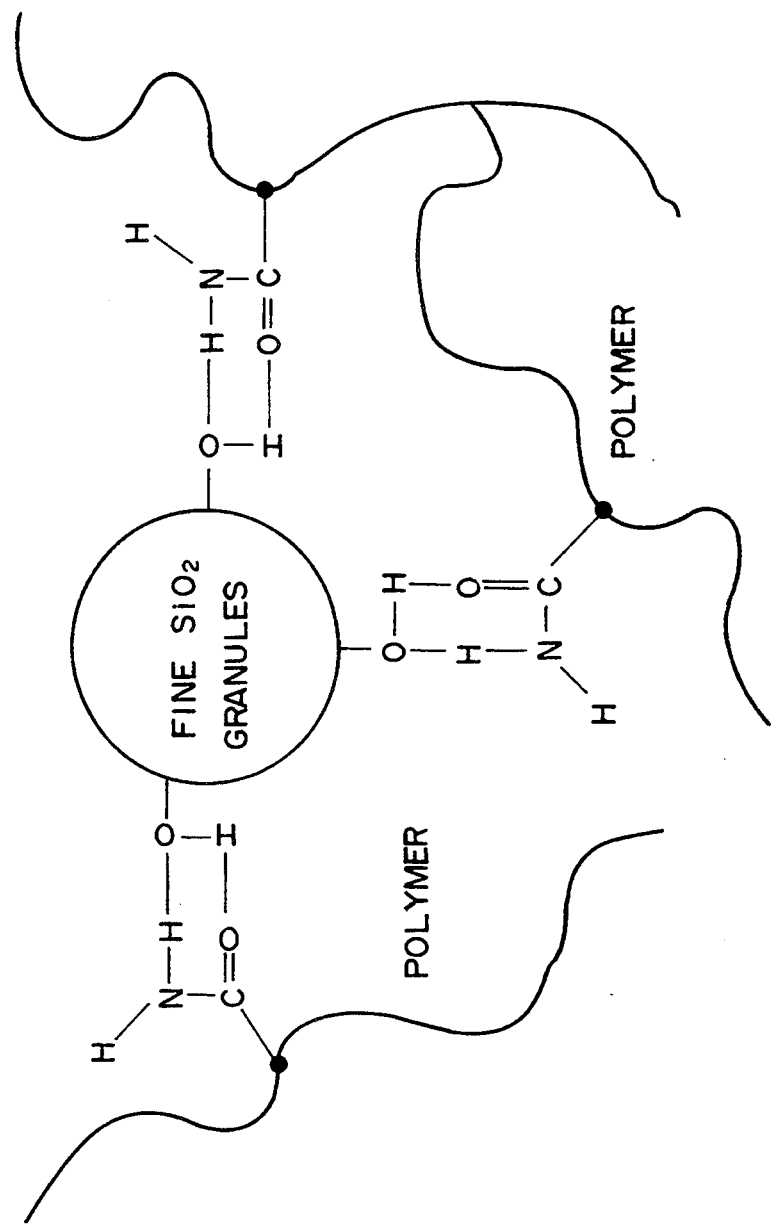
FIG. 4 is a concept diagram showing the bonding of the spherical silica and an acrylamide polymer.

Table 1 shows the properties of this powder and FIG. 1 is an electron microphotograph (SEM) of this powder.

TABLE 1

|  | Example 1 | Comp. Ex. 1 | Comp. Ex. 2 | Comp. Ex. 3 | Comp. Ex. 4 | Comp. Ex. 5 | Comp. Ex. 6 | Comp. Ex. 7 |
|---|---|---|---|---|---|---|---|---|
| Apparent specific gravity (g/ml) | 0.26 | 0.36 | 0.58 | 0.51 | 0.52 | 0.53 | 0.51 | 0.57 |
| Oil-absorbing Amount (ml/100 g) | 192 | 138 | 116 | 108 | 118 | 107 | 96 | 106 |
| Specific surface area (m²/g) | 532 | 580 | 575 | 610 | 335 | 710 | 691 | 523 |
| Pore volume (ml/g) | 0.95 | 0.88 | 0.93 | — | — |  |  |  |
| Yield (%) | 76.4 | 32.1 | 33.7 | 34.4 | 35.0 | 42.0 | 38.5 | 32.8 |
| Grain size |  |  |  |  |  |  |  |  |
| Ave. grain size (μ) | 3.17 | 3.45 | 10.11 | 9.04 | 9.22 | 11.56 | 12.26 | not measureable |
| $D_{25}/D_{75}$ | 1.38 | 2.31 | 3.11 | 3.06 | 3.22 | 3.82 | 4.12 | — |
| SEM grain size (μm) | 2–3 | almost amorphous | amorphous | amorphous | amorphous | amorphous | amorphous | amorphous |
| True sphericality | 93 | — | — | — | — |  |  |  |
| Refractive index | 1.467 | 1.450 | 1.452 | 1.455 | 1.444 |  |  |  |
| Chemical composition (%) |  |  |  |  |  |  |  |  |
| Ig-loss | 5.5 | 6.1 | 5.8 | 6.8 |  |  |  |  |
| $SiO_2$ | 93.7 | 93.4 | 92.0 | 91.9 |  |  |  |  |
| $Al_2O_3$ | 0.16 | 0.18 | 0.16 | 0.14 |  |  |  |  |
| $Na_2O$ | 0.31 | 0.92 | 1.00 | 1.10 |  |  |  |  |
| Filtering property | very good | good | very poor | very poor | poor | very poor | very poor | very poor |
| Remarks | polyacrylamide | sodium alginate | starch, dry product is a hard gel | gelatine, dry product is a hard gel | CMC | PVA, dry product is a hard gel | PEG, dry product is a hard gel | polyamine type organic polymer coagulant dry product is a hard gel |

EXAMPLES 2 AND 3

Fine granular and spherical silica powders were synthesized in the same manner as in Example 1 except that the acrylamide polymer aqueous solution was added in amounts of 14% and 50% reckoned as anhydride with respect to $SiO_2$, and pure water was added thereto in such amounts that the whole amounts were 1500 g.

Table 2 shows the properties of these powders.

TABLE 2

|  | Example 2 | Example 3 | Example 4 | Example 5 | Example 6 | Comp. Ex. 8 |
|---|---|---|---|---|---|---|
| Apparent specific gravity (g/ml) | 0.29 | 0.27 | 0.36 | 0.26 | 0.18 | 0.56 |
| Oil-absorbing Amount (ml/100 g) | 199 | 180 | 170 | 202 | 220 |  |
| Specific surface area (m²/g) | 650 | 590 | 680 | 564 | 390 |  |
| Pore volume (ml/g) | 0.90 | 0.86 | 1.02 | 0.83 | 1.05 |  |
| Yield (%) | 72.6 | 79.3 | 71.5 | 83.6 | 86.7 | 12.1 |
| Grain size |  |  |  |  |  |  |
| Ave. grain size (μ) | 2.89 | 2.78 | 4.32 | 2.20 | 1.78 | 4.82 |
| $D_{25}/D_{75}$ | 1.46 | 1.52 | 1.48 | 1.42 | 1.53 | 3.88 |
| SEM grain size (μm) | 2–3 | 2–3 | 3–4 | 1–2 | 1–1.5 | amorphous |
| True sphericality | 93 | 94 | 97 | 91 | 93 | — |
| Refractive index | 1.464 | 1.470 | 1.462 | 1.473 | 1.461 |  |
| Chemical composition (%) |  |  |  |  |  |  |
| Ig-loss | 6.4 | 6.8 | 5.9 | 7.1 | 6.2 |  |
| $SiO_2$ | 92.8 | 91.8 | 93.6 | 91.9 | 92.8 |  |
| $Al_2O_3$ | 0.12 | 0.14 | 0.10 | 0.11 | 0.13 |  |
| $Na_2O$ | 0.51 | 0.61 | 0.28 | 0.63 | 0.37 |  |
| Filtering property | very good | very good | very good | very good | very good | very poor |
| Remarks |  |  |  |  |  | dry product is a hard gel |

EXAMPLES 4 TO 6

Fine granular and spherical silica powders were synthesized in the same manner as in Example 1 with the exception of setting the stand-still temperature to 2° C., 40° C. and 80° C., respectively.

Table 2 shows the properties of these powders and FIG. 5 is a SEM photograph of the powder synthesized at 2° C.

EXAMPLE 7

A fine granular and spherical silica powder was synthesized in the same manner as in Example 1 except that the stand-still temperature was set at 2° C., the aqueous solution of acrylamide polymer was added in an amount of 10% reckoned as an anhydride with respect to $SiO_2$, the stand-still time was 48 hours, and pure water was added in such an amount that the whole amount was 1500 g.

Table 3 shows the properties of this powder.

EXAMPLES 8 AND 9

Fine granular and spherical silica powders were synthesized in the same manner as in Example 1 with the exception of changing the amount of sodium silicate to 370 g (5.5% of $SiO_2$ concentration) and to 269 g (4% of $SiO_2$ concentration), respectively, and adding pure water in such amounts that the whole amounts were 1500 g.

Table 3 shows the properties of these powders.

EXAMPLE 10

A fine granular and spherical silica powder was synthesized in the same manner as in Example 1 except that sodium silicate (24,0% of $SiO_2$ component and 9.9% of $Na_2O$ component) was added in an amount of 438 g, 7% sulfuric acid was added in an amount of 540 g, and pure water was added in such an amount that the total amount was 1500 g.

Table 3 shows the properties of this powder.

EXAMPLES 11 AND 12

Fine granular and spherical silica powders were synthesized in the same manner as in Example 1 with the exception of using aqueous solutions of polyacrylamides having weight average molecular weights of 300,000 and 1,200,000, respectively, and having a degree of anions of 0.3 mol %.

EXAMPLE 13

A fine granular and spherical silica powder was synthesized in the same manner as in Example 1 with the exception of using a mixed acid (286 g of 7% sulfuric acid + 86 g of 7% hydrochloric acid) instead of using 7% sulfuric acid, and adding pure water in such an amount that the whole amount was 1500 g.

Table 3 shows the properties of this powder.

TABLE 3

|  | Example 7 | Example 8 | Example 9 | Example 10 | Example 11 | Example 12 | Example 13 |
| --- | --- | --- | --- | --- | --- | --- | --- |
| Apparent specific gravity (g/ml) | 0.38 | 0.29 | 0.32 | 0.27 | 0.35 | 0.30 | 0.24 |
| Oil-absorbing Amount (ml/100 g) | 142 | 191 | 188 | 213 | 168 | 195 | 225 |
| Specific surface area ($m^2/g$) | 573 | 683 | 542 | 486 | 577 | 490 | 580 |
| Pore volume (ml/g) | 0.88 | 0.96 | 0.79 | 0.82 | 0.76 | 1.01 | 0.92 |
| Yield (%) | 75.2 | 71.8 | 72.8 | 75.8 | 81.6 | 83.4 | 87.3 |
| Grain size |  |  |  |  |  |  |  |
| Ave. grain size ($\mu$) | 10.79 | 2.89 | 3.21 | 2.44 | 3.45 | 2.77 | 2.58 |
| $D_{25}/D_{75}$ | 1.77 | 1.68 | 1.71 | 1.62 | 1.51 | 1.46 | 1.60 |
| SEM grain size ($\mu m$) | 8–12 | 1–2 | 1.5–2.5 | 1–2 | 2–3 | 2–3 | 2–3 |
| True sphericality | 97 | 91 | 90 | 92 | 95 | 92 | 93 |
| Refractive index | 1.462 | 1.466 | 1.463 | 1.470 | 1.467 | 1.462 | 1.466 |
| Chemical composition (%) |  |  |  |  |  |  |  |
| Ig-loss | 5.8 |  |  |  | 6.5 | 5.8 |  |
| $SiO_2$ | 93.3 |  |  |  | 92.7 | 93.0 |  |
| $Al_2O_3$ | — |  |  |  | 0.16 | 0.12 |  |
| $Na_2O$ | 0.54 |  |  |  | 0.32 | 0.52 |  |
| Filtering property | very good | very good | good | good | very good | good | good |
| Remarks |  |  |  |  |  |  |  |

EXAMPLE 14

A fine granular and spherical silica powder was synthesized in the same manner as in Example 1 with the exception of adding 10.5 g of NaCl into 7% sulfuric acid.

Figure 6:
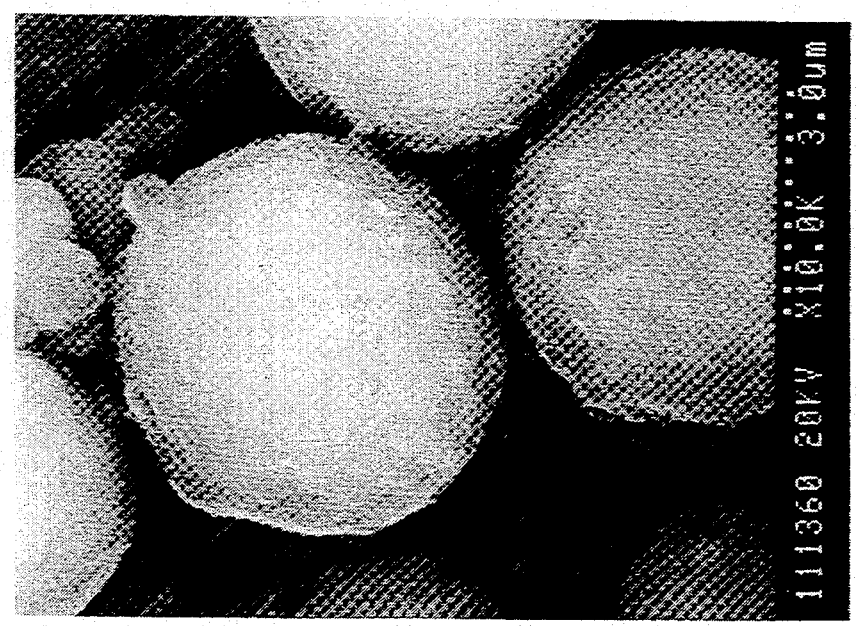
FIG. 6 is a scanning electron microphotograph of a magnification of 10,000 times showing the granular structure of fine spherical silica granules obtained in Example 14 of the present invention.

Table 4 shows the properties of this powder and FIG. 6 is an SEM photograph of this powder.

EXAMPLE 15

A fine granular and spherical silica powder was synthesized in the same manner as in Example 1 with the exception of adding 21 g of $Na_2CO_3$ into the sodium silicate.

Table 4 shows the properties of this powder.

EXAMPLES 16 AND 17

Pure water was added in an amount of 500 ml to 500 g of spherical silica hydrogels prepared in Examples 1 and 5, respectively. The mixtures were introduced into small pressurized vessels having a content of about one liter, and were subjected to the hydrothermal treatment at 150° C. for 2 hours with stirring.

Figure 7:
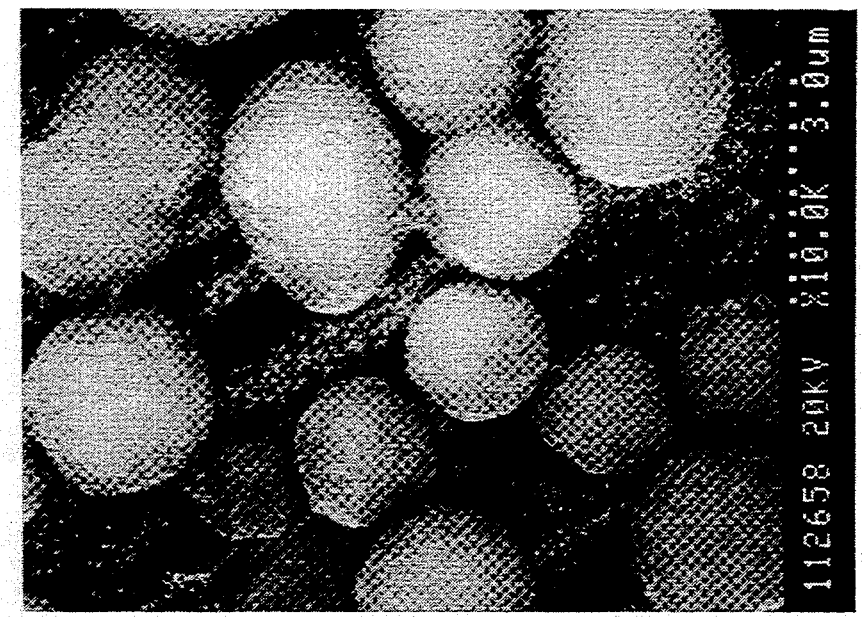
FIG. 7 is a scanning electron microphotograph of a magnification of 10,000 times showing the granular structure of fine spherical silica granules obtained in Example 17 of the present invention.

Table 4 shows the properties of these powders and FIG. 7 is an SEM photograph of Example 17.

TABLE 4

|  | Example 14 | Example 15 | Example 16 | Example 17 |
| --- | --- | --- | --- | --- |
| Apparent specific gravity (g/ml) | 0.38 | 0.28 | 0.19 | 0.17 |
| Oil-absorbing Amount (ml/100 g) | 146 | 188 | 210 | 204 |
| Specific surface area ($m^2/g$) | 620 | 650 | 152 | 170 |
| Pore volume (ml/g) | 0.79 | 0.98 | 0.32 | 0.38 |
| Yield (%) | 93.8 | 90.4 | — | — |

TABLE 4-continued

| | Example 14 | Example 15 | Example 16 | Example 17 |
|---|---|---|---|---|
| Grain size | | | | |
| Ave. grain size ($\mu$) | 4.56 | 3.32 | 3.11 | 2.13 |
| $D_{25}/D_{75}$ | 1.48 | 1.45 | 1.43 | 1.50 |
| SEM grain size ($\mu$m) | 3–4 | 2–3 | 2–3 | 1–2 |
| True sphericality | 94 | 92 | 91 | 91 |
| Refractive index | 1.462 | 1.460 | 1.461 | 1.463 |
| Chemical composition (%) | | | | |
| Ig-loss | 6.8 | 6.0 | | |
| $SiO_2$ | 92.8 | 93.1 | | |
| $Al_2O_3$ | — | — | | |
| $Na_2O$ | 0.20 | 0.42 | | |
| Filtering property | very good | good | good | good |
| Remarks | | | | |

COMPARATIVE EXAMPLES 1 TO 7

Silica granules were prepared in the same manner as in Example 1 but adding a solution of 4% of sodium alginate (Comparative Example 1), a solution of 5% of starch (MS-4600 produced by Nippon Shokuhin Kako) (Comparative Example 2), a solution of 5% of gelatine (Comparative Example 3), a solution of 3% of CMC (Comparative Example 4), a solution of 4% of PVA (PVA-117 produced by Kurare Co.) (Comparative Example 5), a solution of a spolyethylene glycol No. 400 (produced by Wako Junyaku): water=1:3 (Comparative Example 6), and a solution of −1% of a polyamide-type high molecular coagulant (Mw=8,000,000) (Comparative Example 7) instead of adding the aqueous solution of polyacrylamide of Example 1, without effecting the neutralization with an acid, but washing the granules with a dilute acid and repetitively washing them with hot water. As a result, all of them exhibited very poor filtering property, and spherical granules having uniform shapes were not obtained.

Figure 9:
FIG. 9 is a scanning electron microphotograph of a magnification of 10,000 times showing the structure of a silica powder obtained in Comparative Example 2.
Figure 8:
FIG. 8 is a scanning electron microphotograph of a magnification of 10,000 times showing the structure of a silica powder obtained in Comparative Example 1.
Figure 11:
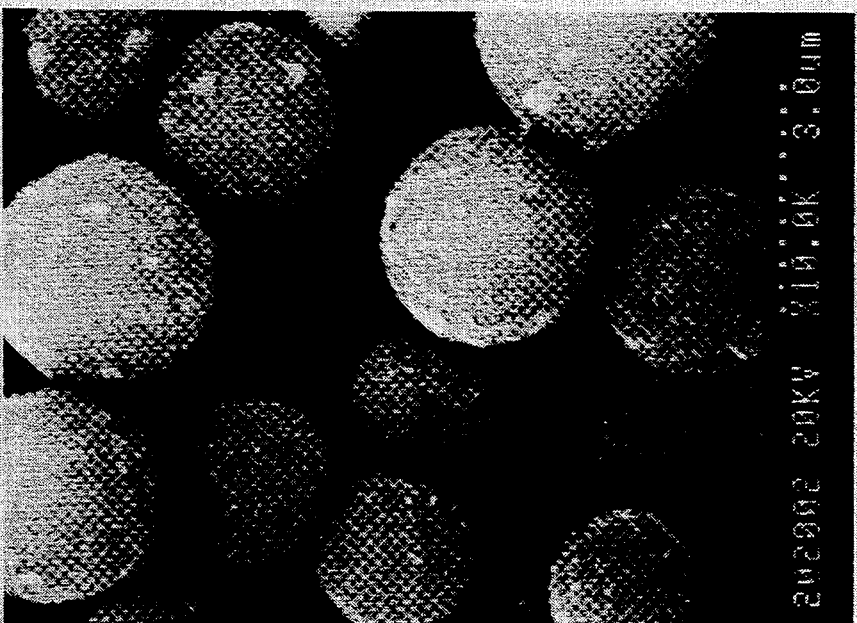
FIG. 11 is a scanning electron microphotograph of a magnification of 10,000 times showing the structure of spherical silicate granules obtained according to the present invention.
Figure 10:
FIG. 10 is a scanning electron microphotograph of a magnification of 10,000 times showing the structure of a silica powder obtained in Comparative Example 3.
Figure 12:
FIG. 12 is a scanning electron microphotograph of a magnification of 10,000 times showing the structure of spherical silicate granules of the present invention blended in a PP film.
Figure 13:
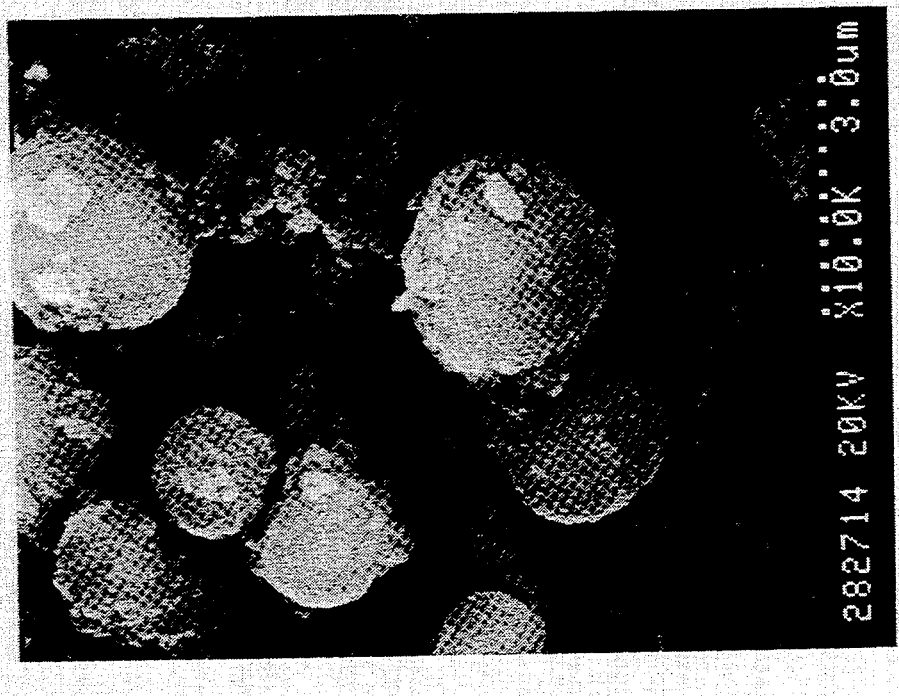
FIG. 13 is a scanning electron microphotograph of a magnification of 10,000 times showing the structure of precursor granules of the present invention blended in the PP film.
Figure 14:
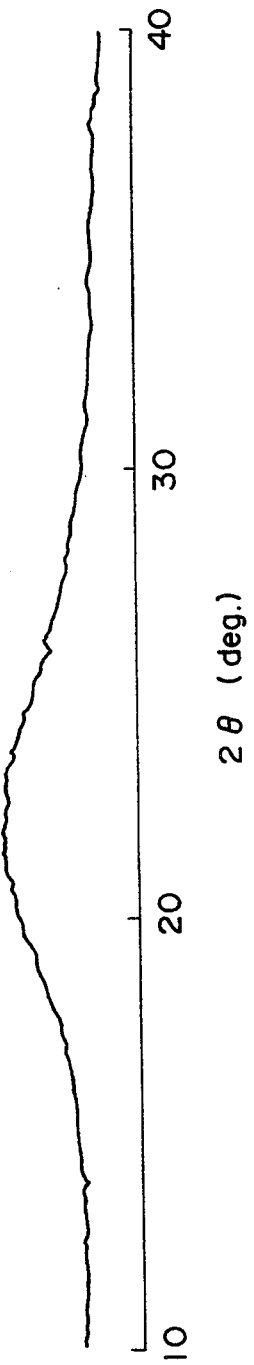
FIG. 14 is an X-ray diffraction diagram of a typical amorphous material (calcium silicate)
Figure 15:
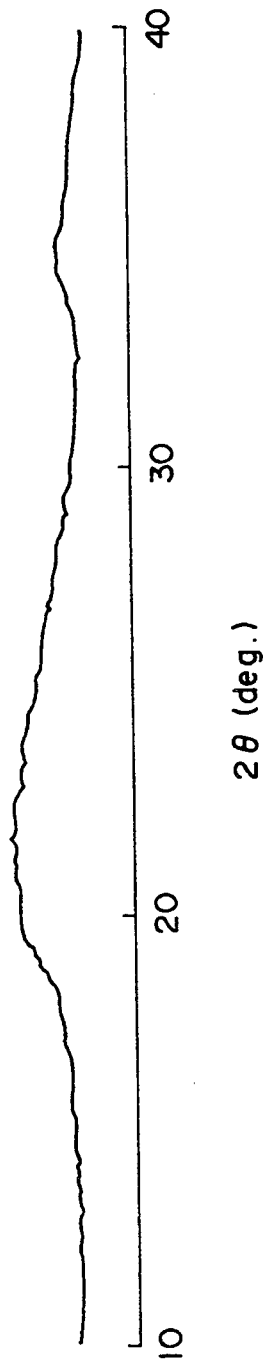
FIG. 15 is an X-ray diffraction diagram of a laminar fine crystalline material (magnesium phyllosilicate.

Table 1 shows the properties of these powders and FIGS. 8, 9 and 10 are SEM photographs of Comparative Examples 1, 2 and 3.

COMPARATIVE EXAMPLE 8

The silica powder was synthesized in the same manner as in Example 1 with the exception of adding the aqueous solution of acrylamide polymer in an amount of 3% reckoned as an anhydride with respect to the $SiO_2$ component and adding pure water in such an amount that the total amount was 1500 g. However, there were not obtained spherical granules having uniform shapes, and the yield was very small.

Table 2 shows the properties of this powder.

COMPARATIVE EXAMPLES 9 AND 10

The procedure of Example 1 was repeated but using sodium silicate in an amount of 673 g (10% of $SiO_2$ concentration) and in an amount of 135 g (2% of $SiO_2$ concentration), respectively, and adding pure water in such amounts that the whole amounts were 1500 g. When the $SiO_2$ concentration was adjusted to 10%, the product gelled and coagulated upon the addition of sulfuric acid. When the $SiO_2$ concentration was adjusted to 2%, the product was not gelled even after 48 hours have passed, and the obtained powder was vitreous and hard.

COMPARATIVE EXAMPLE 11

The silica powder was synthesized in the same manner as in Example 1 with the exception of adding 7% sulfuric acid in an amount of 600 g and adding pure water in such an amount that the whole amount was 1500 g. However, the product gelled prior to adding sulfuric acid (pH dropped to 10.11) and there were not obtained spherical silica having uniform shapes.

COMPARATIVE EXAMPLES 12

The reaction was effected in the same manner as in Example 1 but adding 7% sulfuric acid in an amount of 200 g and adding pure water in such an amount that the whole amount was 1500 g. The product, however, was not gelled even after 48 hours had passed. The pH was 11.22 at the time when the addition of sulfuric acid was finished.

COMPARATIVE EXAMPLE 13

The reaction was effected in the same manner as in Example 1 but using a polyacrylamide having a weight average molecular weight of 8,000,000 at a concentration of 1% and adding pure water in such an amount that the whole amount was 1500 g. However, the product could not be separated by filtration and spherical granules having uniform shapes were not obtained.

Preparation of precursor 1

Into a 15-liter stainless steel container were introduced 3.2 kg of sodium silicate No. 3 (containing 21.9% of $SiO_2$ component and 7.1% of $Na_2O$ component) (7% of $SiO_2$ concentration in the whole solution) and 2.2 kg of pure water. The mixture was then introduced into a constant temperature bath adjusted to 15° C., followed by the addition of 2.1 kg of an acrylamide polymer aqueous solution (about 10% aqueous solution, weight average molecular weight 500,000) (30% reckoned as a polyacrylamide anhydride with respect to $SiO_2$) with mild stirring using a high stirrer, so that the mixture was sufficiently dispersed.

Then, 2.5 kg of 5% sulfuric acid adjusted to 15° C. was added thereto (pH was 10.8 after the addition was finished). After the addition has been finished, the stirring was discontinued, and the mixture was left to stand still for 12 hours. The mixture was then filtered, and the obtained silica cake was dispersed again in pure water, and 5% sulfuric acid was added thereto until the pH reached 2.0. After the pH was nearly stabilized at 2.0, the mixture was stirred for 2 hours, and was then filtered, and washed with water. Furthermore, the cake was repulped to prepare a slurry of spherical silica granules of a concentration of 15% (sample 1—1).

The cake was then dried at 110° C. and was pulverized in a sample mill to obtain a porous and spherical silica powder having a grain size of about 2 to 3 $\mu$m (sample 1-2).

Figure 16:
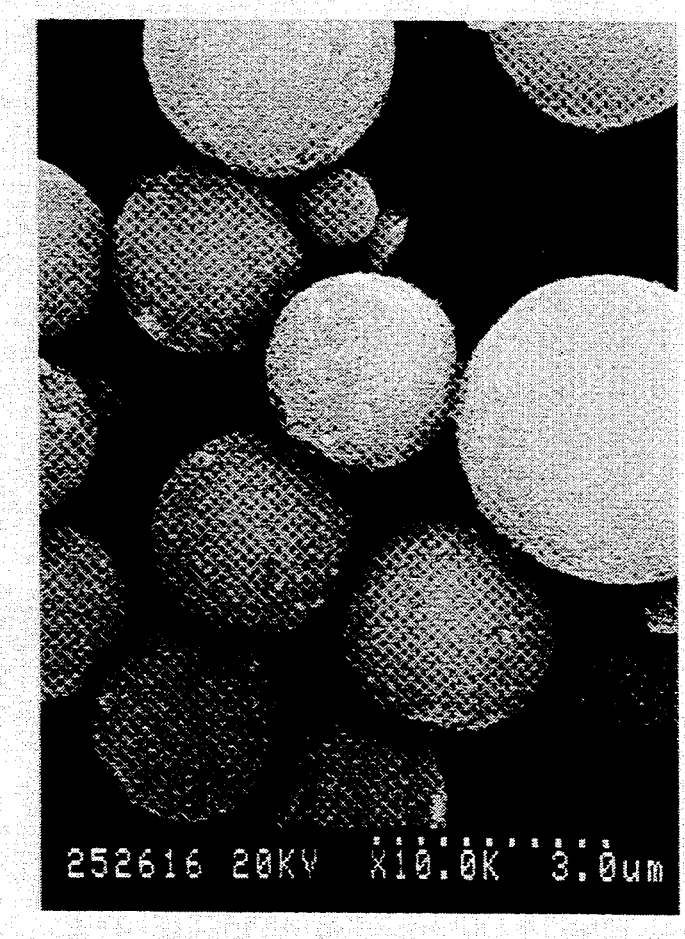
FIG. 16 is a scanning electron microphotograph of a magnification of 10,000 times showing the structure of precursor granules (sample 1-2) of the present invention.
Figure 17:
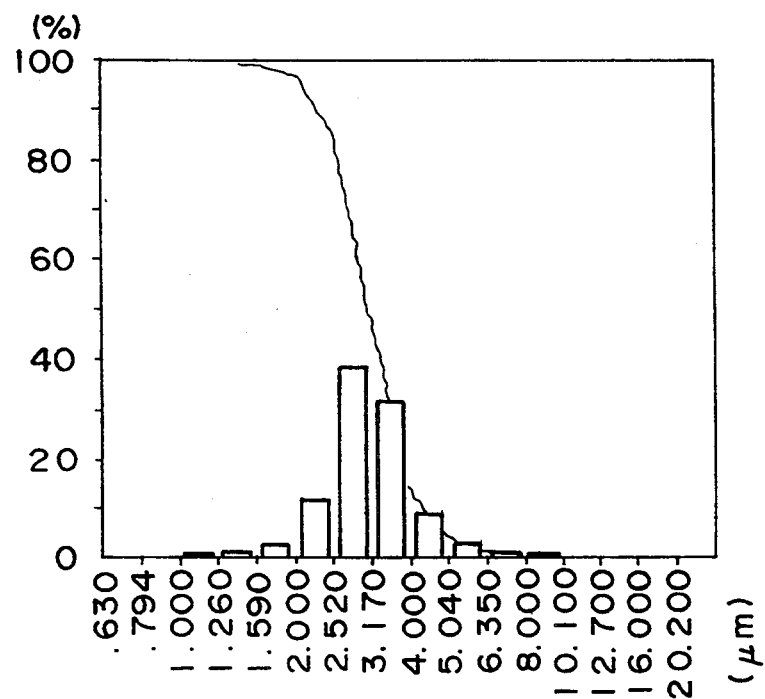
FIG. 17 is a diagram showing a volume-based grain size distribution of the precursor granules of the present invention.
Figure 18:
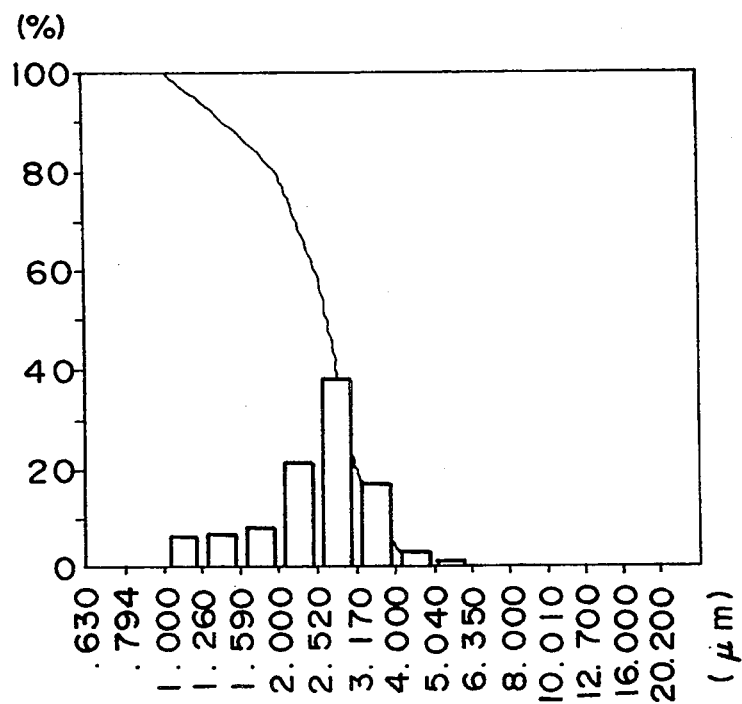
FIG. 18 is a diagram showing a number-based grain size distribution of the precursor granules of the present invention.

Table 5 shows the properties of this powder and FIG. 16 is an electron microphotograph (SEM) of this powder.

EXAMPLES 18 to 21

Into 1-liter of a stainless steel beaker were introduced 800 g of the slurry of sample 1—1, and then powders of magnesium hydroxide (No. 200 produced by Kamishima Kagaku) were added thereto in amounts of 5, 10, 20 and 40%, respectively reckoned as MgO with respect to the solid component of the slurry, dispersed sufficiently, and then heated up to 98° C. in a hot bath. The mixtures were then treated at that temperature for 8 hours, filtered, washed with water, dried at 110° C., pulverized in a sample mill, and were then baked at 400° C. for one hour to obtain porous and spherical magnesium silicate powders.

Table 5 shows the properties of these powders.

EXAMPLE 22

Into a 1-liter stainless steel beaker were introduced 120 g of the sample 1-2, followed by the addition of pure water in such an amount as to obtain a slurry of concentration 15% and a powder of magnesium hydroxide (No. 200 produced by Kamishima Kagaku) in an amount of 30% reckoned as MgO with respect to the solid component of the powder. After being sufficiently dispersed, the mixture was heated up to 98° C. in a hot both and was treated at that temperature for 8 hours, filtered, washed with water, dried at 110° C., pulverized in a sample mill, and was then baked at 400° C. for one hour to obtain a spherical and porous magnesium silicate powder.

Table 5 shows the properties of this powder.

EXAMPLES 23 to 25

The powders were prepared in the same manner as in Example 22 but using a barium hydroxide, a calcium hydroxide, and a strontium hydroxide, respectively each in an amount of 15% reckoned as BaO, CaO, SrO instead of using the magnesium hydroxide that was used in Example 22. Table 5 shows the properties of these powders.

EXAMPLE 26

Instead of the magnesium hydroxide used in Example 22, a zinc hydroxide was added in an amount of 20% reckoned as ZnO. The mixture was then introduced into an autoclave having a volume of one liter, heated at 180° C. and was treated (under a pressure of about 9 kg/cm$^2$) for 5 hours with stirring.

Through washing with water, drying, pulverization and baking carried out in the same manner as in Example 22, there was obtained a spherical zinc silicate powder. Table 5 shows the properties of this powder.

EXAMPLE 27

Example 22 was repeated except that magnesium hydroxide was added in an amount of 10%, reckoned as MgO, and zinc hydroxide was added in an amount of 20%, reckoned as ZnO. The mixture was then introduced into an autoclave having a volume of one litter, heated at 180° C. and was treated (under a pressure of about 9 kg/cm$^2$) for 5 hours with stirring.

Through washing with water, drying, pulverization and baking carried out in the same manner as in Example 22, there was obtained a spherical zinc magnesium silicate powder. Table 5 shows the properties of this powder.

COMPARATIVE EXAMPLE 14

A magnesium silicate powder was prepared in the same manner as in Example 18 but adding the powder of magnesium hydroxide (No. 200 produced by Kamishima Kagaku) in an amount of 60% reckoned as MgO with respect to the solid component of the slurry of sample 1—1. However, the granules coagulated so conspicuously that the spherical shapes could not be maintained.

Preparation of spherical silica granules 2

Into a 15-liter stainless steel container were introduced 3.2 kg of sodium silicate No. 3 (containing 21.9% of SiO$_2$ component and 7.1% of Na$_2$O component (7% of SiO$_2$ concentration in the whole solution) and 2.2 kg of pure water. The mixture was then introduced into a constant temperature bath adjusted to 25° C., followed by the addition of 2.1 kg of an acrylamide polymer aqueous solution (about 10%-concentration aqueous solution, weight average molecular weight 1,000,000, ionization degree 10%) (30% reckoned as a polyacrylamide anhydride with respect SiO$_2$) with mild stirring using a high stirrer, so that the mixture was sufficiently dispersed.

Thereafter, through the same procedure as in "Preparation of spherical silica granules 1", there was obtained a porous and spherical silica granular powder having a grain diameter of about 1 to 1.5 μm (sample 2).

Table 5 shows the properties of this powder.

EXAMPLES 28 AND 29

A spherical and porous magnesium silicate granular powder was obtained in the same manner as in Example 22 but introducing 120 g of the sample 2 into a one-liter stainless steel beaker, adding pure water in such an amount that a slurry of a concentration of 15% was obtained, and adding with stirring the powders of magnesium hydroxide (No. 200 produced by Kamishima Kagaku) in amounts of 5% and 20%, respectively reckoned as MgO with respect to the solid component of the powder.

Table 5 shows the properties of this powder.

Preparation of spherical silica granules 3

Into a 15-liter stainless steel container were introduced 3.65 kg of sodium silicate No. 3 (containing 21.9% of SiO$_2$ component and 7.1% of Na$_2$O component) (7% of SiO$_2$ concentration in the whole solution) and 1.95 kg of pure water. The mixture was then introduced into a constant temperature bath adjusted to 15° C. followed by the addition of 1.6 kg of an acrylamide polymer aqueous solution (about 10%-concentration aqueous solution, weight average molecular weight 500,000, ionization degree 0.5) (20% reckoned as a polyacrylamide anhydride with respect to SiO$_2$) with mild stirring using a high stirrer, so that the mixture was sufficiently dispersed.

Then, 2.8 kg of 5% sulfuric acid adjusted at 15° C. was added thereto. After the addition has been finished, the stirring was discontinued, and the mixture was left to stand still for 48 hours. The mixture was then filtered, and the obtained silica cake was dispersed again in pure water, and 5% sulfuric acid was added thereto until pH reached 2.0. After the pH was nearly stabilized at 2.0, the mixture was stirred for 2 hours, and was then filtered, washed with water, dried, pulverized and baked in the same manner as in the "Preparation of spherical silica granules 1" thereby to obtain a porous and spherical silica granular powder having a grain size of from about 8 to about 10 μm (sample 3).

Table 5 shows the properties of this powder.

EXAMPLES 30 AND 31

A spherical and porous magnesium silicate granular powder was obtained in the same manner as in Example 22 but introducing 120 g of the sample 3 into a one-liter stainless steel beaker, adding pure water in such an amount that a slurry of 15% concentration was obtained, and adding with stirring the powders of magnesium hydroxide (No. 200 produced by Kamishima Kagaku) in amounts of 5% and 25%, respectively, reckoned as MgO with respect to the powdery solid component.

Table 5 shows the properties of these powders.

EXAMPLE 32

Pure water was added to 50 g of the powder obtained in Example 26 thereby to prepare a slurry of spherical zinc silicate granules of a solid content concentration of 10%.

Then, an aluminum chloride solution Al concentration, reckoned as 5% of $Al_2O_3$ and a caustic soda solution of a concentration of 4% were simultaneously added, maintaining a pH value of from 7 to 9 over a period of one hour, to the slurry that was heated at 50° C. with stirring to carry out the coating reaction. After the reaction, the reaction product was stirred and aged for one hour. Thereafter, through the same procedure as in Example 22, there was obtained a spherical zinc silicate powder coated with an aluminum compound.

Table 5 shows the properties of this powder.

TABLE 5

|  | Sample 1-2 | Example 18 | Example 19 | Example 20 | Example 21 | Example 22 | Example 23 | Example 24 | Example 25 |
|---|---|---|---|---|---|---|---|---|---|
| Apparent specific gravity (g/ml) | 0.26 | 0.35 | 0.39 | 0.46 | 0.54 | 0.48 | 0.62 | 0.54 | 0.60 |
| Oil-absorbing amount (ml/100 g) | 198 | 184 | 170 | 128 | 109 | 122 | 86 | 101 | 80 |
| Specific surface area ($m^2$/g) | 421 | 168 | 280 | 341 | 418 | 605 | 84 | 102 | 75 |
| Pore volume (ml/g) | 1.01 | 0.58 | 0.61 | 0.56 | 0.50 | 0.56 | 0.32 | 0.25 | 0.29 |
| Crystal form by X-ray diffraction | amorphous | amorphous | amorphous | phillo-silicate | phillo-silicate | phillo-silicate | amorphous | amorphous | amorphous |
| Grain size distribution |  |  |  |  |  |  |  |  |  |
| Average $D_{50}$ (μm) | 2.86 | 2.56 | 2.70 | 2.88 | 2.86 | 2.90 | 2.86 | 2.74 | 2.66 |
| $D_{25}/D_{75}$ | 1.45 | 1.42 | 1.50 | 1.66 | 1.71 | 1.73 | 1.56 | 1.60 | 1.49 |
| SEM grain size (μm) | 2–3 | 2–3 | 2–3 | 2–3 | 2–3 | 2–3 | 2–3 | 2–3 | 2–3 |
| True sphericality | 0.97 | 0.94 | 0.96 | 0.96 | 0.91 | 0.92 | 0.96 | 0.90 | 0.92 |
| Refractive index | 1.460 | 1.472 | 1.478 | 1.493 | 1.510 | 1.505 | 1.487 | 1.486 | 1.487 |
| Amount worn out | 1 | 3 | 4 | 8 | 12 | 8 | 9 | — | — |
| Chemical composition (mg %) |  |  |  |  |  |  |  |  |  |
| Ig-loss | 5.1 | 4.8 | 5.9 | 7.6 | 5.0 | 6.8 | — | 5.8 | — |
| $SiO_2$ | 94.8 | 90.1 | 84.0 | 73.3 | 56.5 | 62.3 | 80.8 | 90.1 | 80.9 |
| $Al_2O_3$ | 0.05 | — | — | — | — | — | — | — | — |
| $Na_2O$ | 0.05 | — | — | 0.03 | — | 0.03 | — | — | — |
| MgO | — | 4.9 | 10.1 | 18.9 | 38.4 | 30.8 | — | — | — |
| MO | — | — | — | — | — | — | BaO 15.2 | CaO 13.9 | SrO 14.7 |
| Remarks | SEM (FIG. 6) |  |  | SEM (FIG. 1) |  |  |  |  |  |

|  | Example 26 | Example 27 | Sample 2 | Example 28 | Example 29 | Sample 3 | Example 30 | Example 31 | Example 32 |
|---|---|---|---|---|---|---|---|---|---|
| Apparent specific gravity (g/ml) | 0.67 | 0.66 | 0.22 | 0.30 | 0.42 | 0.32 | 0.38 | 0.52 | 0.48 |
| Oil-absorbing amount (ml/100 g) | 112 | 120 | 202 | 180 | 134 | 184 | 173 | 126 | 138 |
| Specific surface area ($m^2$/g) | 318 | 296 | 472 | 176 | 329 | 431 | 158 | 326 | 368 |
| Pore volume (ml/g) | 0.60 | 0.52 | 0.98 | 0.70 | 0.52 | 1.11 | 0.78 | 0.51 | 0.56 |
| Crystal form by X-ray diffraction | amorphous | phillo-silicate | amorphous | amorphous | phillo-silicate | amorphous | amorphous | phillo-silicate | phillo-silicate |
| Grain size distribution |  |  |  |  |  |  |  |  |  |
| Average $D_{50}$ (μm) | 2.56 | 2.89 | 1.65 | 1.70 | 1.77 | 11.22 | 10.70 | 10.51 | 2.70 |
| $D_{25}/D_{75}$ | 1.66 | 1.72 | 1.62 | 1.66 | 1.70 | 1.52 | 1.48 | 1.70 | 1.89 |
| SEM grain size (μm) | 2–3 | 2–3 | 1–1.5 | 1–1.5 | 1–1.5 | 8–10 | 8–10 | 8–10 | 2–3 |
| True sphericality | 0.94 | 0.88 | 0.92 | 0.92 | 0.88 | 0.93 | 0.94 | 0.88 | 0.85 |
| Refractive index | 1.500 | 1.502 | 1.461 | 1.476 | 1.492 | 1.461 | 1.474 | 1.500 | 1.498 |
| Amount worn out | 8 | — | 2 | 4 | 7 | — | — | — | — |
| Chemical composition (%) |  |  |  |  |  |  |  |  |  |
| Ig-loss | — | — | 5.4 | — | — | 5.3 | — | — | — |
| $SiO_2$ | 75.8 | 65.8 | 94.5 | 91.1 | 74.3 | 94.3 | 90.0 | 70.1 | 73.2 |
| $Al_2O_3$ | — | — | 0.05 | — | — | 0.05 | — | — | 4.6 |
| $Na_2O$ | , | — | 0.03 | — | — | 0.06 | — | — | — |
| MgO | — | — | — | — | 5.1 | 19.8 | — | — | — |
| MO | ZnO 19.1 | (MgO) 9.8 (ZnO) 18.3 | — | — | — | — | MgO 4.8 | MgO 25.1 | ZnO 16.9 |
| Remarks |  |  |  |  |  |  |  |  |  |

TABLE 6

| No. | Blending agent | Blending amount (ppm) | Haze (%) | Blocking property | Fish eye | Scratching property |
|---|---|---|---|---|---|---|
| 1 | Example 5 | 500 | 2.7 | ◯ | 1 | ◯ |
| 2 | Example 5[1)] | 500 | 2.0 | ◯ | 2 | ◯ |
| 3 | Example 5[2)] | 500 | 2.2 | ◯ | 2 | ◯ |

TABLE 6-continued

| No. | Blending agent | Blending amount (ppm) | Haze (%) | Blocking property | Fish eye | Scratching property |
|---|---|---|---|---|---|---|
| 4 | Example 17 | 500 | 2.5 | ○ | 2 | ○ |
| 5 | Example 17[1)] | 500 | 1.9 | ○ | 1 | ○ |
| 6 | Example 17[2)] | 500 | 2.1 | ○ | 4 | ○ |
| 7 | Example 17[3)] | 500 | 2.3 | ○ | 3 | ○ |
| 8 | Commercially available[4)] synthetic silica | 500 | 3.6 | Δ | 18 | Δ |

[1)] Product whose surfaces are treated with 3% of a silane coupling agent (A-1100 produced by Nippon Unika).
[2)] 200 Parts of a terpene resin (Crearon P-105 produced by Yasuhara Yushi) are added to a silica powder, and the mixture is fully melted, kneaded, cooled, and is then pulverized into smaller than 1 mm.
[3)] Granular powder is coated with 20% of erucic amide.
[4)] Blended in an amount equal to the weight of the silica granules.

TABLE 7

| No. | Blending agent | Blending amount (ppm) | Haze (%) | Blocking property | Fish eye | Scratching property |
|---|---|---|---|---|---|---|
| 1 | Example 20 | 800 | 2.4 | ○ | none | 0.6 |
| 2 | Example 28 | 800 | 2.2 | ○ | 2 | 0.3 |
| 3 | Example 29 | 800 | 2.0 | ○ | none | 0.5 |
| 4 | Example 29[1)] | 800 | 1.8 | ○ | none | 0.4 |
| 5 | Example 29[2)] | 800 | 2.0 | ○ | none | 0.4 |
| 6 | Example 29[3)] | 800 | 1.8 | ○ | none | 0.2 |
| 7 | Example 29[4)] | 800 | 1.9 | ○ | none | 0.5 |
| 8 | Sample 1-2 | 800 | 3.2 | Δ | 8 | 0.2 |
| 9 | Sample 2 | 800 | 3.1 | Δ | 5 | 0.2 |
| 10 | Commercially available[5)] synthetic silica | 800 | 5.8 | X | 19 | 1.2 |

[1)] Product whose surfaces are treated with 3% of a silane coupling agent (A-1100 produced by Nippon Unika).
[2)] Granular powder is coated with 40% of erucic amide (Alflo P-10 produced by Nippon Yushi).
[3)] 200 Parts of a terpene resin (Crearon P-105 produced by Yusuhara Yushi) are added to a silicate powder, and the mixture is fully melted, kneaded, cooled and is then pulverized into smaller than 1 mm.
[4)] 200 Parts of a PP wax (Viscol 550P produced by Sanyl Kasei) are added to a silicate powder, and the mixture is fully melted, kneaded, cooled, and is pulverized into smaller than 1 mm.
[5)] Blended in an amount equal to the weight of the silicate powder.

APPLICATION EXAMPLE 1

Application to a biaxially drawn polypropylene film

To 100 parts by weight of a polypropylene resin powder (Hipole F657P produced by Mitsui Petrochemical Co.) were added 0.15 parts of a 2,6-ditertiary butyl-paracresol, 0.1 part of calcium stearate and additives shown in Tables 6 and 7. The mixture was mixed together by a super mixer for one minute and was them melted, mixed and pelletized by using a monoaxial extruder at a kneading temperature of 230° C.

By using a T-die, the pellets were formed into a green film which was then drawn into 5 times in the vertical direction and 10 times in the lateral direction through a biaxial drawing molding machine to obtain biaxially drawn films having thicknesses of 25 and 30 μm.

Then, the thus obtained films were subjected to the following tests. The results were as shown in Tables 6 and 7.

Haze: Measured by using automatic digital haze meter, model NDH-20D manufactured by Nippon Denshoku Co. in compliance with JIS K-6714.

Blocking property: Two films are placed one upon the other and are left to stand at 40° C. for 24 hours with the application of a load of 200 g/cm², and are evaluated as follows depending upon their degree of peeling:
ⓞ Peels easily
○ Peels not to easily.
Δ Peels not easily.
X Peels very little Fish eyes: Expressed in terms of a number of dots greater then 0.1 mm in 400 cm² of the film as observed through an optical microscope.

Scratching property: After 5 hours from the preparation of the films, two films are placed one upon the other and are rubbed with each other with fingers, and are evaluated as follows depending upon their degree of being scratched.
o Not almost scratched
○ Scratched to a small degree
Δ Scratched a little.
X Scratched.

Or, the scratching property is found from a difference of the haze before and after the rubbing by applying a load of 10 kg onto the films having a section 10×10 cm, rubbing them together three times, and measuring the haze.

APPLICATION EXAMPLE 2

Application to an undrawn polypropylene film

To 100 parts by weight of a polypropylene resin powder were added 0.15 parts of a 2,6-ditertiary butyl-paracresol, 0.1 part of the calcium stearate, and additives of Tables 8 and 9. The mixture was mixed together by a super mixer for one minute and was melted, mixed and pelletized by using a monoaxial extruder at a kneading temperature of 230° C. By using a T-die, the pellets were formed at the same temperature into undrawn films having thicknesses of 25 to 30 μm.

The thus obtained films were evaluated in the same manner as in Application Example 1. The results were as shown in Tables 8 and 9.

TABLE 8

| No. | Blending agent | Blending amount (ppm) | Haze (%) | Blocking property | Fish eye | Scratching property |
|---|---|---|---|---|---|---|
| 1 | Example 1 | 1400 | 2.1 | ○ | 2 | ○ |
| 2 | Example 1[1] | 1400 | 2.0 | ○ | 4 | ○ |
| 3 | Example 1[2] | 1400 | 2.0 | ○ | 2 | ○ |
| 4 | Example 4 | 1200 | 1.9 | ○ | 1 | ○ |
| 5 | Example 16 | 1400 | 2.1 | ○ | 3 | ○ |
| 6 | Example 16[1] | 1400 | 1.8 | ○ | 5 | ○ |
| 7 | Example 16[3] | 1400 | 2.0 | ○ | 3 | △ |
| 8 | Example 16[4] | 1400 | 2.3 | ○ | 4 | ○ |
| 9 | Commercially available[5] synthetic silica | 1400 | 3.2 | X | 20 | △ |

[1] Product whose surface are treated with 2% of a silane coupling agent (A-1100 produced by Nippon Unika).
[2] 100 Parts of a terpene resin (Crearon P-105 produced by Yasuhara Yushi) are added to a silica powder, and the mixture is fully melted, kneaded, cooled, and is pulverized into smaller than 1 mm.
[3] Granular silica powder is coated with 10% of erucic amide.
[4] Silica granules are coated with 15% of hydrotalcite.
[5] Blended in an amount equal to the weight of the silica granules.

TABLE 9

| No. | Blending agent | Blending amount (ppm) | Haze (%) | Blocking property | Fish eye |
|---|---|---|---|---|---|
| 1 | Example 19 | 2,000 | 3.2 | ○ | none |
| 2 | Example 19[1] | 2,000 | 2.6 | ○ | none |
| 3 | Example 19[2] | 2,000 | 2.4 | ○ | 1 |
| 4 | Example 19[3] | 2,000 | 3.1 | ○ | 2 |
| 5 | Example 30 | 2,000 | 3.0 | ○ | none |
| 6 | Sample 1-2 | 2,000 | 4.8 | X | 14 |
| 7 | Commercially available[4] synthetic silica | 2,000 | 5.1 | X | 24 |

[1] Product whose surfaces are treated with 2% of a silane coupling agent (A-1100 produced by Nippon Unika).
[2] Granular powder is coated with 40% of erucic amide (Alflo P-10 produced by Nippon Yushi).
[3] Granular are coated with 15% of hydrotalcite.
[4] Blended in an amount equal to the weight of the silicate powder.

APPLICATION EXAMPLE 3

Application to a polyethylene film

Samples shown in Tables 10 and 11 were added to a mixture of a linear low-density polyethylene having an MI of 1.3 g/10 min. and a density of 0.92 and a low-density polyethylene having an MI of 1.1 g/10 min. and a density of 0.93, and the mixtures were melted, mixed and pelletized using an extruder at a temperature of 180° C.

The pellets were then fed to an extruder, inflation-formed into films of a thickness of 30 μm. The thus obtained films were evaluated in the same manner as in Application Example 1. The results were as shown in Tables 10 and 11.

TABLE 10

| No. | Blending agent | Blending amount (%) | Haze (%) | Blocking property | Gloss | Fish eye | Scratching property |
|---|---|---|---|---|---|---|---|
| 2 | Example 1 | 0.30 | 4.7 | ○ | 126 | 2 | ○ |
| 3 | Example 1[1] | 0.30 | 4.9 | ○ | 112 | 5 | ○ |
| 4 | Example 1[2] | 0.30 | 5.0 | ○ | 110 | 4 | ○ |
| 5 | Example 1[3] | 0.30 | 4.1 | ○ | 127 | 6 | ○ |
| 6 | Example 1[4] | 0.30 | 3.7 | ○ | 130 | 2 | ○ |
| 7 | Example 4 | 0.25 | 4.6 | ○ | 122 | 3 | ○ |
| 8 | Example 16 | 0.30 | 4.9 | ○ | 120 | 5 | ○ |
| 9 | Example 16[4] | 0.30 | 4.1 | ○ | 128 | 4 | ○ |
| 13 | Synthetic zeolite | 0.30 | 5.2 | △ | 107 | 18 | △ |

*Contains 0.08% of calcium stearate and 0.08% of erucic amide.
[1] Commercially available talc (average grain diameter 3.4μ) is added in an amount of 15%.
[2] Commercially available diatomaceous earth (average grain diameter 3.7μ) is added in an amount of 15%.
[3] Silica granules are coated with 10% of hydrotalcite.
[4] Silica granules are coated with 10% of erucic amide.

TABLE 11

| No. | Blending agent | Blending amount (%) | Haze (%) | Blocking property | Gloss | Fish eye |
|---|---|---|---|---|---|---|
| 1 | Example 20 | 0.50 | 4.8 | ○ | 123 | none |
| 2 | Example 20[1] | 0.50 | 4.6 | ○ | 116 | 2 |
| 3 | Example 20[2] | 0.50 | 5.1 | ○ | 108 | 3 |
| 4 | Example 20[3] | 0.50 | 5.4 | ○ | 109 | 2 |
| 5 | Example 20[4] | 0.50 | 4.8 | ○ | 118 | none |
| 6 | Example 20[5] | 0.50 | 4.1 | ○ | 125 | none |
| 7 | Example 22 | 0.50 | 4.7 | ○ | 120 | none |
| 8 | Example 23 | 0.50 | 4.5 | ○ | 121 | none |
| 9 | Sample 1-2 | 0.50 | 7.7 | X | 102 | 14 |

TABLE 11-continued

| No. | Blending agent | Blending amount (%) | Haze (%) | Blocking property | Gloss | Fish eye |
|---|---|---|---|---|---|---|
| 10 | Synthetic zeolite[6] | 0.50 | 7.8 | X | 98 | 11 |

*Contains 0.08% of calcium stearate and 0.08% of erucic amide.
[1] Commercially available talc (average grain diameter 3.4μ) is added in an amount of 15%.
[2] Commercially available diatomaceous earth (average grain diameter 3.7μ) is added in an amount of 15%.
[3] Commercially available kaolin (average grain diameter 3.4μ) is added in an amount of 15%.
[4] Granules are coated with 10% of hydrotalcite.
[5] Granules are coated with 40% of erucic amide.
[6] Blended in an amount equal to the weight of the silicate powder.

APPLICATION EXAMPLE 4

Application to a heat-sensitive recording paper

Solutions for forming heat-sensitive recording layers of the following composition were prepared by using the samples shown in Table 12, applied in a coating amount of 7 g/m² onto an undercoating paper using a bar coater No. 8, dried by the air, and were subjected to calendering under a pressure of 5 kg/m² to prepare heat-sensitive recording papers.

| | |
|---|---|
| Dye slurry | 10 parts |
| Developer slurry | 20 parts |
| Sensitizer slurry | 20 parts |
| Binder | 15 parts |
| Sample | 20 parts |

Then, by using the FAX-510T of NTT, a test chart No. 1 of the Japanese Association of Image Electronics was copied to develop color on the heat-sensitive recording paper, and the color concentration was measured by using a densitometer FSD-103 (manufactured by Fuji Photofilm Co.).

Colorless portions were also measured and indicated as ground color.

As for the scum adhesion testing, an inked ribbon was removed from a PC-PRIOITL Japanese Language color heat-transfer printer of NEC, and a heat-sensitive recording paper for testing was printed solid black. At this moment, the adhesion of scum on the thermal head was observed and evaluated as follows:
° No adhesion
○ Slightly adhered
Δ Adhered to some extent
X Adhered seriously The results were as shown in Table 12.

TABLE 12

| No. | Blending agent | Color concentration | Scum adhesion | Ground color |
|---|---|---|---|---|
| 1 | Example 6 | 1.47 | ⊚ | 0.13 |
| 2 | Example 17 | 1.45 | ⊚ | 0.12 |
| 3 | Commercially available synthetic silica | 1.45 | ○ | 0.13 |
| 4 | Calcium carbonate | 1.21 | X | 0.25 |

APPLICATION EXAMPLE 5

Application to an ink-jet paper

To 10 g of the samples (dried at 110° C.) shown in Table 13 were added 25 g of an aqueous solution of 15% of a polyvinyl alcohol (PVA 117 of Kuraray Co.) as a binder and water in such an amount that the whole amount was 60 g. The mixture were sufficiently stirred and dispersed using a stirrer to prepare coating solutions.

The coating solutions were applied in a coating amount of 10 g/m² onto a base paper (paper for PPC) having a basis weight of 45 g/m² to obtain recording papers.

The thus obtained recording papers were set to an ink-jet color image printer (10-0700 manufactured by Sharp Co.) connected to a personal computer (CP-9801 manufactured by Nippon Electric Co.) to obtain hard copy recording papers with a test pattern.

The image planes of the obtained hard copy test papers printed in four colors of Black (IN-0011), Magenta (IN-0012), Cyan (IN-0013) and Yellow (IN-0014) were irradiated with light from an ultraviolet-ray lamp (253.7 nm, GL-15 manufactured by Tokyo Shibaura Denki Co.) for 14 hours maintaining a distance of 10 cm between the lamp and the test pieces. The color fading degrees of the test pieces were compared by naked eyes and were evaluated on the following basis. The results were as shown in Table 13.

TABLE 13

| No. | Blending agent | Black | Magenta | Cyan | Yellow |
|---|---|---|---|---|---|
| 1 | Example 1 | ⊚ | ○ | ○ | ⊚ |
| 2 | Example 4 | ⊚ | ○ | ⊚ | ⊚ |
| 3 | Example 14 | ⊚ | ○ | ○ | ⊚ |
| 4 | Commercially available synthetic silica | Δ | X | X | ○ |

⊚ Colors did not almost fade compared to before being irradiated and the image maintained vividness.
○ Colors faded slightly compared to before being irradiated but the image still maintained vividness.
Δ Colors faded compared to before being irradiated and the image lost vividness.
X Colors faded very greatly compared to before being irradiated.

APPLICATION EXAMPLE 6

Samples shown in Table 14 were added to an acryl urethan paint (Deepblack) No. 400 produced by Kanpe Co.). The mixtures were dispersed for 5 minutes in a high-speed homo-mixer (2500 rpm) and were applied onto glass plates maintaining a film thickness of 150 μm by using a film applicator of 5 mil, and were measured for their 60-degree mirror surface reflection factor, smoothness and scratching property.

As for the scratching property, the film was rubbed with a coin and the scratched condition was observed.

TABLE 14

| No. | Blending agent (amount added, %) | 60° Gloss | Smoothness | Scratching property |
|---|---|---|---|---|
| 1 | Example 1 (3%) | 26.8 | good | ○ |
| 2 | Example 4 (3%) | 24.9 | good | ○ |
| 3 | Example 14 (3%) | 25.0 | good | ○ |
| 4 | Commercially available synthetic | 25.6 | good | X |

TABLE 14-continued

| No. | Blending agent (amount added, %) | 60° Gloss | Smoothness | Scratching property |
|---|---|---|---|---|
|  | silica (3%) |  |  |  |

○ Almost no scratch
Δ Scratched a little
X Scratched considerably

APPLICATION EXAMPLE 7

Application to a powder foundation

Powder foundations of the following recipe were prepared by using the sample obtained in Example 1.

| Components (A) | |
|---|---|
| Mica | 38 parts |
| Talc | 10 parts |
| Titanium dioxide | 18 parts |
| Pigment | 5 parts |
| Spherical silica | 15 parts |

| (Example 1) Components (B) | |
|---|---|
| Squalene | 5 parts |
| Lanolin | 4 parts |
| Isopropyl myristate | 3 parts |
| Surfactant | 1 part |
| Perfume | suitable amount |

Mica, Talc, titanium dioxide, coloring pigment and spherical silica of the components (A) were weighed in amounts of parts mentioned above, introduced into a stainless steel container, sufficiently mixed together, and were pulverized by an atomizer.

The mixture was then sufficiently mixed together by using a Henschel's mixer, and to which a heated mixture of the components (B) was added, followed by sufficient mixing to obtain a product.

Then, the thus obtained foundation and a foundation not containing spherical silica were tested by ten randomly selected persons ranging in age from 30 to 50 years old. All persons claimed that the foundation containing spherical silica spread well, was smooth and finished well.

APPLICATION EXAMPLE 8

Films having a thickness of 30 μm were prepared by adding the samples shown in Table 15 in the same manner as in Application Example 3. Next, the films of a size of B5 (182×257 mm) to which the samples have been added were introduced into a 1.8-liter glass bottle which was then hermetically sealed.

Then, standard gases ($NH_3$, $H_2S$) were introduced by using a micro syringe so that their concentrations were 100 ppm. The films were left to stand still at 25° C. and the concentrations of the residual gases were measured by a gas chromatography after 3 hours and 10 hours have passed to find the amounts of adsorption.

Moreover, the odors of the films were compared by the direct functional test and were expressed as follows:

○ Almost no odor of resin
Δ A small degree of odor of resin
χ Strong odor of resin The results were as shown in Table 15.

TABLE 15

| No. | Blending agent | Blending amount (%) | Haze (%) | Reduction of $NH_3$ (%) 3 Hours | Reduction of $NH_3$ (%) 10 Hours | Reduction of $H_2S$ (%) 3 Hours | Reduction of $H_2S$ (%) 10 Hours |
|---|---|---|---|---|---|---|---|
| 1 | Example 22 | 1.0 | 6.2 | 15 | 37 | 18 | 59 |
| 2 | Example 26 | 1.0 | 6.9 | 18 | 44 | 31 | 62 |
| 3 | Example 27 | 1.0 | 6.4 | 17 | 46 | 28 | 77 |
| 4 | Example 27 | 3.0 | 8.1 | 29 | 53 | 42 | 89 |
| 5 | Example 32 | 0.5 | 5.8 | 21 | 43 | 31 | 76 |
| 6 | Example 32 | 1.0 | 6.9 | 39 | 71 | 56 | 94 |
| 7 | Sample 1-2 | 1.0 | 9.4 | 7 | 18 | 7 | 16 |
| 8 | No addition (blank) | 0 | 3.8 | 4 | 12 | 5 | 15 |

APPLICATION EXAMPLE 9

Sheets were prepared by using a paste-type vinyl chloride resin to which have been added an azo-type foaming agent to reduce the weight and the samples shown in Table 16. The odor-trapping (deodorizing) properties of the sheets were evaluated by the direct functional test. The results were as shown in Table 16.

Vinyl chloride sheet blending:

|  | parts by weight |
|---|---|
| Paste-type vinyl chloride resin | 100 |
| Trioctyltrimellitate | 70 |
| Dimethyltin bis(2-ethylhexyl ester thioglycolate) | 2 |
| Foaming agent | 0.1 |
| Zeolite | 0 to 10 |
| Samples (Table 16) | 0.01 to 10 |

TABLE 16

| No. | Sample name | Blending amount (parts by weight) | Amount of zeolite added (parts by weight) | Odor when sheet is prepared | Odor of vinyl chloride sheet |
|---|---|---|---|---|---|
| 1 | Example 26 | 2.0 | 1.5 | none | none |
| 2 | Example 27 | 2.0 | 2.0 | none | none |
| 3 | Example 27 | 6.0 | 2.0 | none | none |
| 4 | No addetion | 0 | 2.0 | yes | a little |

We claim:

1. A process for producing porous and spherical silica granules comprising mixing an aqueous solution of an alkali silicate, an acrylamide polymer and an aqueous solution of an acid of a partly neutralizing amount together, leaving the mixture solution to stand to form a granular material composed of a partly neutralized product of the alkali silicate, and separating the granular material followed by neutralization with an acid.

2. A process for producing porous and spherical silica granules according to claim 1, wherein the alkali silicate is a sodium silicate having a composition, $$Na_2O \cdot mSiO_2$$

wherein m is a number of from 1 to 4.

3. A process for producing porous and spherical silica granules according to claim 1, wherein the acrylamide polymer is the one having a weight average molecular weight of from 10,000 to 3,000.000.

4. A process for producing porous and spherical silica granules according to claim 1, wherein the acrylamide polymer has carboxyl groups of a free form or of the form of a salt at a concentration of from 0.2 to 50 millimols/100 g.

5. A process for producing porous and spherical silica granules according to claim 1, wherein the alkali silicate is made present in the mixture solution at a concentration of 2 to 10% by weight reckoned as $SiO_2$.

6. A process for producing porous and spherical silica granules according to claim 1, wherein the acrylamide polymer is added in an amount of 5 to 100% by weight based on $SiO_2$.

7. A process for producing porous and spherical silica granules according to claim 1, wherein in effecting the neutralization, the acid is added in such an amount that the pH of the mixture solution is from 10 to 11.2.

8. A process for producing porous and spherical silicate granules according to claim 7, wherein a precursor composed of the amorphous silica granular material of partly or completely neutralized product of the alkali silicate obtained by using the acrylamide polymer as a coagulation growing agent is reacted with a hydroxide or a salt of a metal of the Group II of periodic table in an aqueous solvent.

9. A process for producing porous and spherical silicate granules according to claim 8, wherein the precursor of amorphous silica and the hydroxide or the salt of a metal (M) of the Group II of periodic table are reacted together at a weight ratio of $SiO_2:MO=99:1$ to 50:50.

10. A process for producing porous and spherical silicate granules according to claim 8, wherein the hydroxide of a metal of the Group II of periodic table is a magnesium hydroxide.

11. A process for producing porous and spherical silicate granules according to claim 8, wherein the metal (M) of the Group II of periodic table is zinc.

12. Porous and spherical silica or silicate granules comprising a silica or a silicate having a composition, $SiO_2:MO=99:1$ to 50:50 (wherein M is a metal of the Group II of periodic table) as expressed by a weight ratio based on the oxides, and further having amorphous or fine laminar crystalline property as observed through X-ray diffraction, independent and distinct spherical shapes with a true sphericality expressed by a ratio $D_S/D_L$ of a long diameter $D_L$ to a short diameter $D_S$ of the granules of from 0.8 to 1.0, a BET specific surface area of from 50 to 800 m$^2$/g, a sharpness of granular size distribution defined by the relation.

$$D_{25}/D_{75}$$

wherein $D_{25}$ denotes a grain diameter of 25% value on a volume-based cumulative grain size distribution curve as measured by the Coulter counter method, and $D_{75}$ denotes a grain diameter of 75% value thereof, of from 1.2 to 2.0, and a refractive index of from 1.46 to 1.55 as measured by the solution immersion method.

13. Porous and spherical silica or silicate granules according to claim 12, wherein said granules have a peak of pore volume distribution over the pore radii of from 10 to 100 Å, as well as a pore volume of from 0.2 to 2.0 Ml/g.

14. Porous and spherical silica or silicate granules according to claim 12, wherein the primary grain diameter is from 0.3 to 30 μm as observed through a scanning electron microscope.

15. Porous and spherical silica or silicate granules according to claim 12, wherein the apparent specific gravity (in compliance with the method of JIS K-6220) is from 0.05 to 0.7.

16. Porous and spherical silicate granules according to claim 12, wherein the silicate comprises a magnesium phyllosilicate.

17. Porous and spherical silicate granules according to claim 12, wherein the silicate comprises a zinc phyllosilicate or an aluminum-containing zinc phyllosilicate.

18. An anti-blocking agent for resin films comprising porous and spherical silicate granules which have a composition $SiO_2:MO=99:1$ to 50:50 (wherein M is a metal of the Group II of periodic table), as expressed by a weight ratio based on the oxides, amorphous or fine laminar crystalline property as observed through X-ray diffraction, independent and distinct spherical shapes with a true sphericality expressed by a ratio $D_S/D_L$ of a long diameter $D_L$ to a short diameter $D_S$ of the granules of from 0.8 to 1.0, and a grain diameter of from 0.3 to 20 μm as observed through a scanning electron microscope.

19. A thermoplastic resin film obtained by adding the anti-blocking agent of claim 18 in an amount of from 0.01 to 5 parts by weight per 100 parts by weight of the thermoplastic resin.

20. A filler for ink-jet recording papers comprising porous and spherical silica or silicate granules of claim 12.

21. A filler for resin paints comprising porous and spherical silica or silicate granules of claim 12.

* * * * *